United States Patent
Wolf, II

(10) Patent No.: US 10,045,697 B2
(45) Date of Patent: Aug. 14, 2018

(54) SYSTEM FOR TRANSCUTANEOUS MONITORING OF INTRACRANIAL PRESSURE

(71) Applicant: Erich W. Wolf, II, Lake Charles, LA (US)

(72) Inventor: Erich W. Wolf, II, Lake Charles, LA (US)

(*) Notice: Subject to any disclaimer, the term of this patent is extended or adjusted under 35 U.S.C. 154(b) by 844 days.

(21) Appl. No.: 14/161,282

(22) Filed: Jan. 22, 2014

(65) Prior Publication Data

US 2014/0135647 A1 May 15, 2014

Related U.S. Application Data

(60) Division of application No. 13/645,358, filed on Oct. 4, 2012, now Pat. No. 8,784,332, which is a division of application No. 13/199,105, filed on Aug. 19, 2011, now Pat. No. 8,366,633, which is a division of application No. 11/544,849, filed on Oct. 6, 2006, now Pat. No. 8,057,401, which is a
(Continued)

(51) Int. Cl.
*A61B 5/00* (2006.01)
*A61B 5/03* (2006.01)

(52) U.S. Cl.
CPC .......... *A61B 5/0077* (2013.01); *A61B 5/0017* (2013.01); *A61B 5/0031* (2013.01); *A61B 5/0086* (2013.01); *A61B 5/031* (2013.01); *A61B 5/0075* (2013.01); *A61B 2560/0219* (2013.01); *A61B 2562/0247* (2013.01)

(58) Field of Classification Search
CPC ... A61B 5/0077; A61B 5/0017; A61B 5/0031; A61B 5/031; A61B 5/0086; A61B 5/0075; A61B 2560/0219; A61B 2562/0247
See application file for complete search history.

(56) References Cited

U.S. PATENT DOCUMENTS 1,912,213 A   5/1933  Nicolson
3,308,398 A * 3/1967  Chilton ................. G08C 19/12
                                              324/76.41
(Continued)

*Primary Examiner* — Rene Towa
(74) *Attorney, Agent, or Firm* — Schultz & Associates, P.C.

(57) ABSTRACT

A system for measuring and converting to an observer intelligible form an internal physiological parameter of a patient. The invention allows transcutaneous telemetry of intracranial pressure via a system which includes a patient implanted sensor module and an external processing module, optically coupled to the sensor module via an external coupling module. A sensor within the sensor module transduces the measured pressure and a near infrared emitter transmits the telemetry when interrogated by the external coupling module. A set of tuned inductor-crystal circuits comprised in part of a cylindrical crystal oscillator whose resonant frequency is sensed by a dipper circuit arrangement is provided. Power for the sensor module is derived inductively through rectification of a transcutaneously-applied high-frequency alternating electromagnetic field generated within the external coupling module. A computer within the processing module calculates the physiological parameter from the telemetry signal and represents this data in numerical, graphical, or analog format.

13 Claims, 16 Drawing Sheets

Related U.S. Application Data continuation-in-part of application No. 11/065,428, filed on Feb. 24, 2005, now Pat. No. 7,435,229.

(60) Provisional application No. 60/547,691, filed on Feb. 25, 2004, provisional application No. 60/577,807, filed on Jun. 8, 2004, provisional application No. 60/582,337, filed on Jun. 23, 2004.

(56) References Cited

U.S. PATENT DOCUMENTS

| | | | |
|---|---|---|---|
| 3,488,821 A | 1/1970 | Richards | |
| 3,648,512 A | 3/1972 | Abbotts | |
| 3,672,352 A | 6/1972 | Summers | |
| 4,067,241 A | 1/1978 | Corbett | |
| 4,281,667 A | 8/1981 | Cosman | |
| 4,354,506 A | 10/1982 | Sakaguchie et al. | |
| 4,385,636 A | 5/1983 | Cosman | |
| 4,471,786 A | 9/1984 | Inagaki et al. | |
| 4,495,818 A | 1/1985 | Ikeda et al. | |
| 4,519,401 A | 5/1985 | Ko et al. | |
| 4,550,611 A | 11/1985 | Czamocki | |
| 4,653,508 A | 3/1987 | Cosman | |
| 4,660,568 A | 4/1987 | Cosman | |
| 4,677,982 A | 7/1987 | Llinas et al. | |
| 4,922,745 A | 5/1990 | Rudkin et al. | |
| 5,231,880 A * | 8/1993 | Ward | G01L 9/0022 310/338 |
| 5,345,811 A | 9/1994 | Alexandrovich et al. | |
| 5,437,284 A | 8/1995 | Trimble | |
| 5,704,352 A | 1/1998 | Tremblay et al. | |
| 5,741,246 A | 4/1998 | Prescott | |
| 5,795,307 A | 8/1998 | Krueger | |
| 5,873,840 A * | 2/1999 | Neff | A61B 5/031 343/767 |
| 6,083,174 A | 7/2000 | Brehmeier-Flick et al. | |
| 6,113,553 A | 9/2000 | Chubbuck | |
| 6,162,238 A | 12/2000 | Kaplan et al. | |
| 6,164,284 A | 12/2000 | Schulman et al. | |
| 6,210,346 B1 | 4/2001 | Hall et al. | |
| 6,243,608 B1 * | 6/2001 | Pauly | A61N 1/37217 128/903 |
| 6,442,413 B1 | 8/2002 | Silver | |
| 6,529,759 B1 | 3/2003 | Tucker et al. | |
| 6,533,733 B1 | 3/2003 | Ericson et al. | |
| 6,544,193 B2 | 4/2003 | Abreu | |
| 6,610,096 B2 | 8/2003 | MacDonald | |
| 6,731,976 B2 | 5/2004 | Penn et al. | |
| 2002/0150140 A1 | 10/2002 | Julicher et al. | |
| 2003/0223756 A1 | 12/2003 | Tatum et al. | |
| 2004/0031323 A1 | 2/2004 | Coleman | |
| 2004/0208600 A1 | 10/2004 | Guenter et al. | |
| 2004/0254438 A1 | 12/2004 | Chuck et al. | |
| 2005/0143790 A1 | 6/2005 | Kipke et al. | |
| 2005/0158356 A1 | 7/2005 | Hunter et al. | |
| 2005/0195403 A1 | 9/2005 | Xu et al. | |
| 2006/0115202 A1 * | 6/2006 | Stevens | G01L 9/0042 385/12 |

* cited by examiner

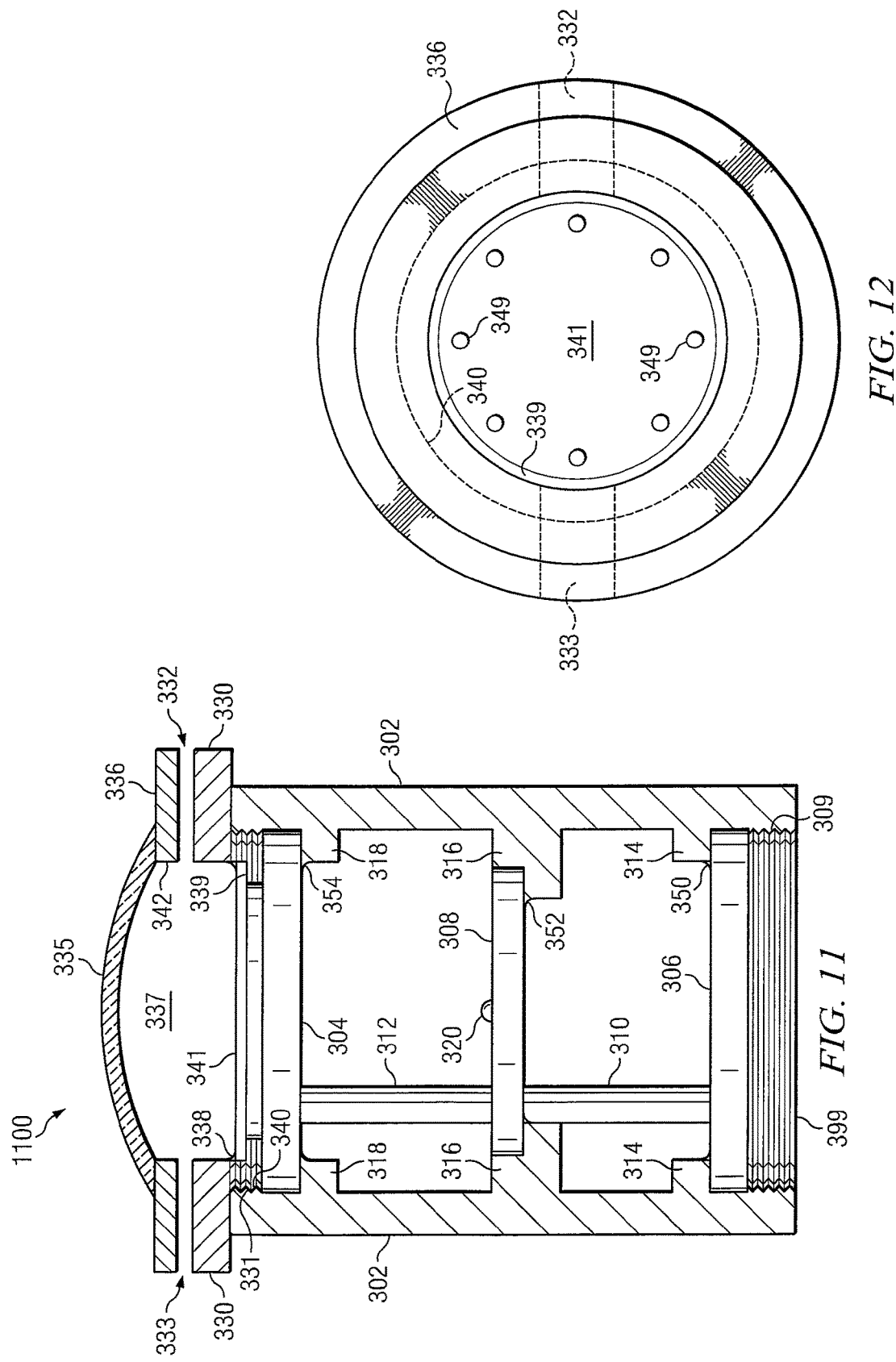

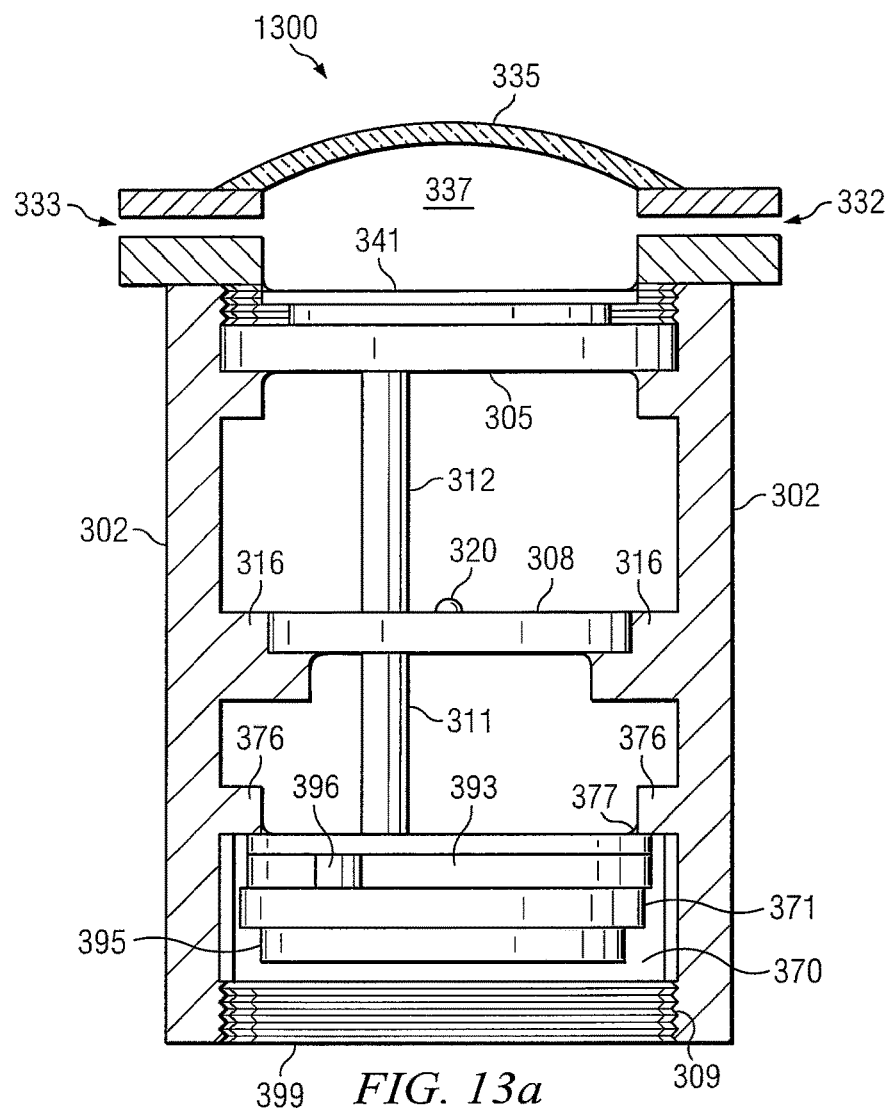
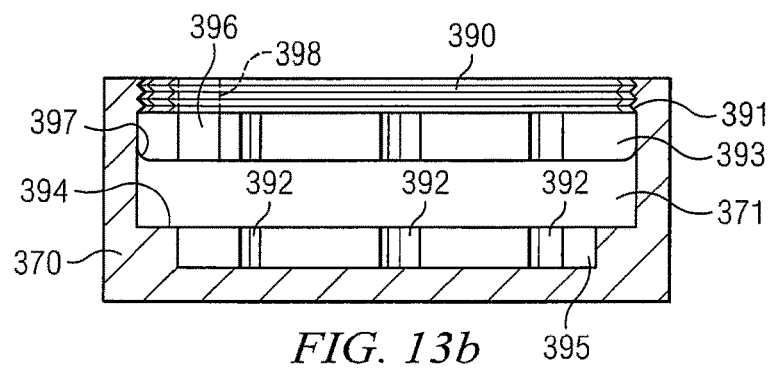
FIG. 13a
FIG. 13b

SYSTEM FOR TRANSCUTANEOUS MONITORING OF INTRACRANIAL PRESSURE

CROSS REFERENCE TO RELATED APPLICATIONS

This application is a Divisional of application Ser. No. 13/645,358, filed Oct. 4, 2012, now pending, which is a Divisional of application Ser. No. 13/199,105, filed Aug. 19, 2011, now U.S. Pat. No. 8,366,633, which is a Divisional of application Ser. No. 11/544,849, filed Oct. 6, 2006, now U.S. Pat. No. 8,057,401, which is a Continuation-in-Part of application Ser. No. 11/065,428, filed Feb. 24, 2005, now U.S. Pat. No. 7,435,229, which claims priority benefit from U.S. Provisional Application Nos. 60/547,691, filed on Feb. 25, 2004, 60/577,807, filed on Jun. 8, 2004, and 60/582,337, filed on Jun. 23, 2004. Each patent application identified above is incorporated here by reference in its entirety to provide continuity of disclosure.

FIELD OF INVENTION

The present inventions relate generally to transcutaneous telemetry with an implantable biomedical device, and more specifically relate to a system for transcutaneous monitoring of intracranial pressure (ICP).

BACKGROUND OF THE INVENTION

The measurement of intracranial pressure (ICP) plays a critical role in several neurosurgical conditions. Various pathological processes such as hydrocephalus, tumors, and trauma can cause alterations in the pressure within the skull. If not adequately controlled, increases in intracranial pressure (due to accumulation of cerebrospinal fluid, blood clots, tumors, or brain swelling) can cause secondary damage to otherwise healthy brain tissue.

A number of technologies currently exist to monitor brain pressure. Many of these rely on invasive techniques with percutaneously implanted sensors. Wires or fiber optic cables are often used to transduce pressure information from electromechanical or optomechanical transducers, which relegates these technologies to short term use. At the end of use these sensors are withdrawn from the body. Several disadvantages are associated with such devices: 1) the presence of a percutaneous probe increases the chance of iatrogenic infections such as meningitis and cerebritis; 2) the probe must be withdrawn at the end of use, and so it is not reusable for subsequent episodes of suspected intracranial hypertension such as with hydrocephalus; and 3) the percutaneous cable is subject to mechanical failure and to inadvertent pull-out during routine patient care.

In an attempt to mitigate these disadvantages, numerous investigators have tried to develop non-invasive techniques for monitoring intracranial pressure. Such methods have employed mathematical correlations between physiological variables which can be transduced extracorporally such as blood pressure, heart rate, Doppler ultrasound of cerebral blood vessels, near-infrared (NIR) spectroscopy of cerebral oxygenation, retinal imaging, etc. While some success has been achieved in monitoring trends in ICP, no method has been fully successful in deriving the absolute intracranial pressure, and these known techniques have not gained significant clinical utility for monitoring ICP.

In another aspect of the present invention, a passive device based on two quiescent resonant tuned circuits is positioned subcutaneously on the patient's skull. While the concept of using a passive device for intracranial pressure monitoring exists in the prior art via Seylar, U.S. Pat. No. 4,114,606, a number of novel improvements are brought to bear in the present invention. In one such improvement, the device compensates for temperature, aging and stray capacitance by using two collocated and implanted circuits, the first circuit in contact with the intracranial space and thus experiencing the intracranial pressure; the second circuit sealed at a fixed and predetermined pressure. In another such improvement, the present invention incorporates a radio frequency identification (RF-ID) tag for holding calibration data and other critical data such as patient information and insertion date.

The presently described invention utilizes near-infrared beams to traverse biological tissue for the digital transmission of data.

Physiological parameters such as tissue oxygenation may be measured by comparing the absorption of specific optical wavelengths by the hemoglobin and cytochrome chromophores. This technology is omnipresent in the hospital setting in the form of pulse oximetry. In what is best disclosed as spectrophotometry, these aforementioned measurement techniques utilize analog means to derive quantitative measures of some physiological parameter via absorption of selected spectra. In a dramatic paradigm shift, the presently described invention utilizes an infrared beam to traverse biological tissue for the digital transmission of data.

The suitability of transmission of data across biological tissues via infrared beam is dependent primarily upon the attenuation of the light beam. From the modified Beer-Lambert equation, the attenuation, expressed in optical density, is:

$$\text{Attenuation}(OD) = -\log(I/Io) = B\mu_a d_p + G \tag{1}$$

Where "I" represents the transmitted light intensity, "Io" represents the incident intensity, "B" is a path length factor dependent upon the absorption coefficient "$\mu_a$" and scattering coefficient "$\mu_s$," "dp" represents the interoptode distance, and G represents a geometry-dependent factor.

The Near Infrared (NIR) spectrum is generally referred to as the frequency range from 750 to 2500 nm. In vivo measurements of NIR absorption during transillumination of the newborn infant brain suggest an optical density of 10 over interoptode distances of 8-9 cm. See, Cope, M and Delpy, D. T. "System for long term measurement of cerebral blood and tissue oxygenation on newborn infants by near infrared transillumination." Medicine, Biology, Engineering and Computing, 26(3):289-94, 1988. Assuming the light source and detector are collinear and antiparallel, the geometry-dependent factor, G, becomes negligible. Because biological tissue is an effective multiple scatterer of light, the effective path length traveled by a given photon can only be estimated. In a study measuring the water absorption peak at 975 nm and assuming average tissue water content, the path length of brain tissue is estimated at 4.3 times the interoptode distance. See, Wray, S., Cope, M., Delpy, D. T., Wyatt, J. S. and Reynolds, E.O.R. "Characterization of the near infrared absorption spectra of cytochrome aa3 and hemoglobin for the non-invasive monitoring of cerebral oxygenation." Biochimica Biophysica Acta 933:184-92, 1988. Thus, from the Beer-Lambert equations, the calculated absorption coefficient for human brain is approximately 0.26 $cm^2$ with an assumed path length of 4.3. This is within the range of absorption coefficients (0.0434-0.456 $cm^2$) quoted in the literature. See, Svaasand, L. O. and Ellingsen, R. "Optical properties of brain." Photochemistry and Photobiology, 38(3):293-9, 1983. In the studies of Tamura and Tamura, extracranial structures such as skin, muscle and bone had minimal effects on the NIR transmission-mode absorbance, presumably because the blood flow and oxygen consumption of these structures is low compared to that of cerebral cortex. See, Tamura, M. and Tamura, T. "Noninvasive monitoring of brain oxygen sufficiency on cardiopulmonary bypass patients by near-infra-red laser spectrophotometry." Medical and Biological Engineering and Computing 32:S151-6. The relatively minor contribution of scalp tissue to NIR absorption is further corroborated by Owen-Reece, Owen-Reece, H., Elwell, C. E., Wyatt, J. S. and Delpy, D. T., "The effect of scalp ischaemia on measurement of cerebral blood volume by near-infrared spectroscopy." Physiological Measurements, November, 17(4): 279-86, 1996. Thus, it is reasonable to expect that for a typical scalp thickness of 1 cm, the absorption would be somewhat less than: $B\mu_a d_p=(4.3)(0.26)(1)=1.1$, assuming that the geometry factor is negligible. Therefore, with an attenuation of one to two orders of magnitude and an NIR emitter output power of 5 mW, the transmitted light intensity is well within the sensitivity range of common silicon photodiodes.

Delpy, et al have investigated the relationship between attenuation and the transit time of light through tissue in an attempt to determine optical path length. See, Delpy, D. T., Cope, M., van der Zee, P., Arridge, S., Wray, S. and Wyatt, J. "Estimation of optical path length through tissue from direct time of flight measurement." Physics, Medicine and Biology 33(12): 1433-42, 1988. Temporal dispersion resulting from spatial and temporal delta functions of the input beam as it passes through scattering tissue may be described by the temporal spread point function (TSPF). Using a Monte Carlo model of light transport in tissue and experimentally derived (in vitro rat brain) scattering phase function at 783 nm, they computed the TSPF for a beam of light passing through a 1 cm thick slab of brain tissue. Estimates of path length based upon the time-of-flight of photons using the TSPF integrated over the exit surface, at all exits angles, and assuming radial symmetry, yields an average path length of 5.3 times the interoptode distance. The final photons to emerge from the tissue are calculated to have traveled 9.2 times the interoptode distance. The temporal dispersion of the light will limit the maximum transmission bandwidth:

$$F_{max}=1/t=c/dn \quad (2)$$

Where $F_{max}$ is the maximum transmission frequency, t is the time for the light to traverse the tissue, c is the speed of light, d is the distance traveled, and n is the refractive index.

SUMMARY OF INVENTION

In one of the embodiments of the present invention, systems and methods are used which allow ad lib transcutaneous telemetry of absolute intracranial pressure via a system which includes a patient implanted sensor module and a processing and display module which is external of the patient and optically coupled to the sensor module via an external coupling module. The sensor module is implanted in much the same fashion as with existing technologies but the skin is closed back over the device and no cabling penetrates the skin. A sensor within the implanted module transduces absolute pressure information and a near infrared (NIR) emitter transmits this telemetry information when interrogated by the complementary external coupling module. Light in the near-infrared spectrum is easily transmitted through the skin and is detected by the external module. Indefinite longevity and small size is attained in the implant by not incorporating a power source within the module. Instead, power is derived inductively through rectification of a transcutaneously-applied high-frequency alternating electromagnetic field which is generated by a power source within the external coupling module, in concept much like a conventional electrical transformer. A computer within the processing and display module calculates the absolute pressure from the NIR telemetry signal and represents these data either in numerical, graphical, or analog format.

The present inventions overcome disadvantages of existing technologies by providing a means for telemetric conveyance of physiological data via transcutaneous projection of a near infrared light beam. The use of this technique for telemetry of intracranial pressure is only one of many potential applications and any reference to intracranial pressure monitoring is not meant to limit the scope of applicability. Furthermore, the transcutaneous telemetry of information is not limited to a unidirectional fashion. Indeed, telemetric data may be transferred bi-directionally between an extra corporeal device and an implanted device. Broadly stated, the implanted device may be a sensor of one or more physiological parameters, contain some form of data unique to the device or unique to the person (or organism) harboring the implant, or may somehow monitor the physiological state of the person (or organism). Specific examples of devices include, but are not limited to, intracranial pressure monitors, tissue oxygen sensors, glucose sensors, neurostimulators, pacemakers, and defibrillators. An extra corporeal device allows recording, display, or interpretation of data from the implanted device and may communicate in bi-directional fashion to convey information back to the implant such as calibration data, handshaking data, etc.

The preferred embodiment of the present invention discloses an implantable biometric sensor system comprising a rigid subcutaneous case, an access portal to an internal fluid in the subcutaneous case, a dual frequency crystal oscillator, affixed to the rigid subcutaneous case and in ducted communication with the internal fluid, for sensing a pressure difference in the internal fluid, and at least one driver coil in electrical communication with the dual frequency crystal oscillator.

The preferred embodiment of the present invention also discloses a method of determining intracranial fluid pressure providing the steps of providing a cylindrical crystal oscillator probe having a transducer section and a reference section, providing at least one driver circuit within the cylindrical crystal oscillator probe connected to the transducer section and the reference section, exposing the reference section to a reference pressure, exposing the transducer section to the intracranial fluid pressure, exciting the transducer section to provide a first frequency energy absorption, exciting the reference section to produce a second frequency energy absorption, measuring the first frequency energy absorption, measuring the second frequency energy absorption, comparing the measurement of the first frequency energy absorption and the second frequency energy absorption to determine a difference, relating the difference to the reference pressure to determine the intracranial fluid pressure, and reporting the intracranial fluid pressure.

BRIEF DESCRIPTION OF DRAWINGS

The disclosed inventions will be described with reference to the accompanying drawings, which show important sample embodiments of the invention and which are incorporated in the specification hereof by reference, wherein:

FIG. 3b is top plan view of the device of FIG. 3a.

FIG. 5b is a plan view of the lower side of the crystal shown in FIG. 5a.

FIG. 11 is a cross-section of a preferred embodiment of the ICP transducer implant.

FIG. 12 is a plan view of a preferred embodiment of the ICP implant.

FIG. 13a is a cross section of a preferred embodiment of the ICP transducer implant.

FIG. 13b is a partial view of the sealed cylindrical enclosure of the invention.

DETAILED DESCRIPTION OF PREFERRED EMBODIMENTS

The numerous innovative teachings of the present application will be described with particular reference to the presently preferred embodiments (by way of example, and not of limitation).

Figure 1:
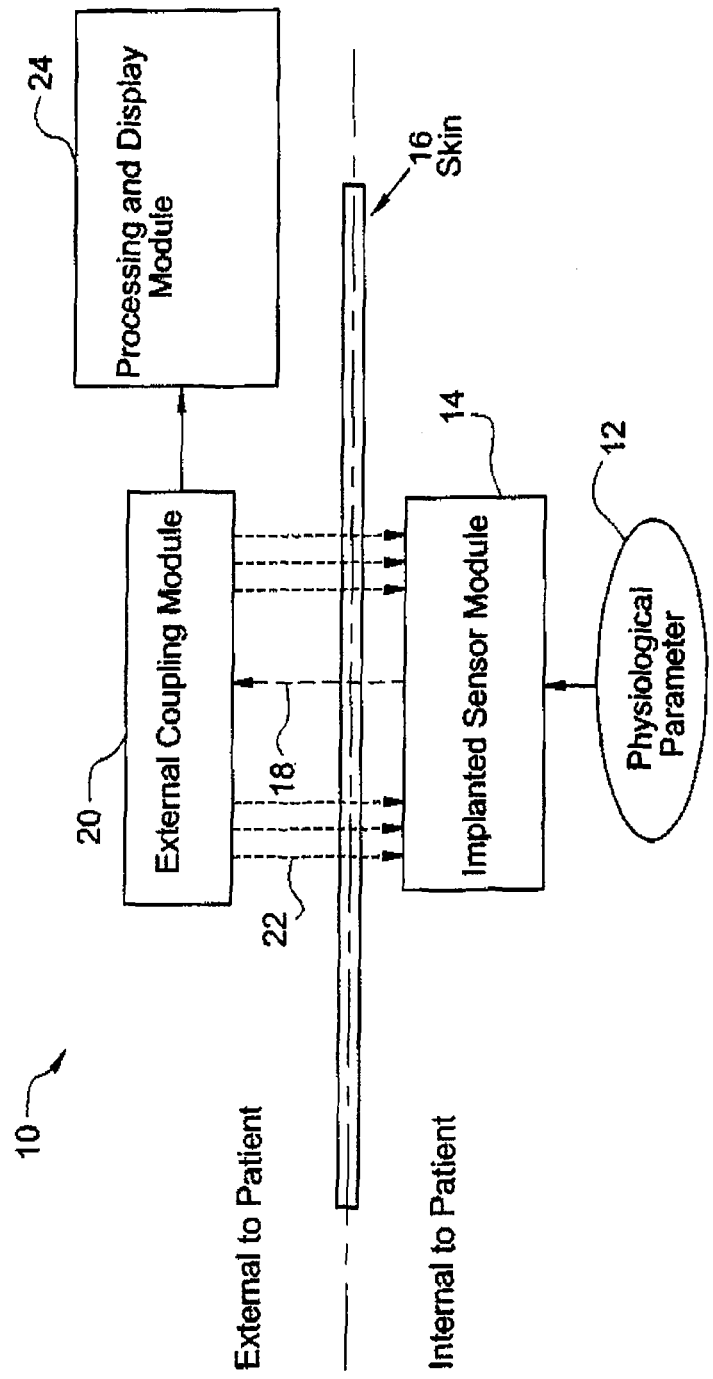
FIG. 1 is a schematic block diagram of a transcutaneous monitoring system in accordance with the present invention.

One embodiment of the present inventions is illustrated by FIG. 1, which shows a schematic block diagram of a transcutaneous monitoring system 10. A physiological parameter 12, such as intracranial pressure, is transduced by an implant 14. The implant is buried beneath the skin 16 of the patient. Information regarding the transduced physiological parameter 12 is converted to a digital form which modulates a near-infrared (NIR) emitter in the implant 14. The modulated NIR telemetry signal 18 emanates from the implant 14, permeates the skin 16 of the patient, and is detected by an external coupling module 20.

Power to the implant 14 is derived inductively through rectification of a transcutaneously-delivered time-varying electromagnetic field 22 which is applied by an external power source via external coupling module 20, in concept much like a conventional electrical transformer. Implant 14 is powered only when in the vicinity of the external coupling module 20. A computer calculates the physiological parameter 12 from the NIR telemetry signal 18 and represents these data either in numerical, graphical, or analog format.

Figure 2:
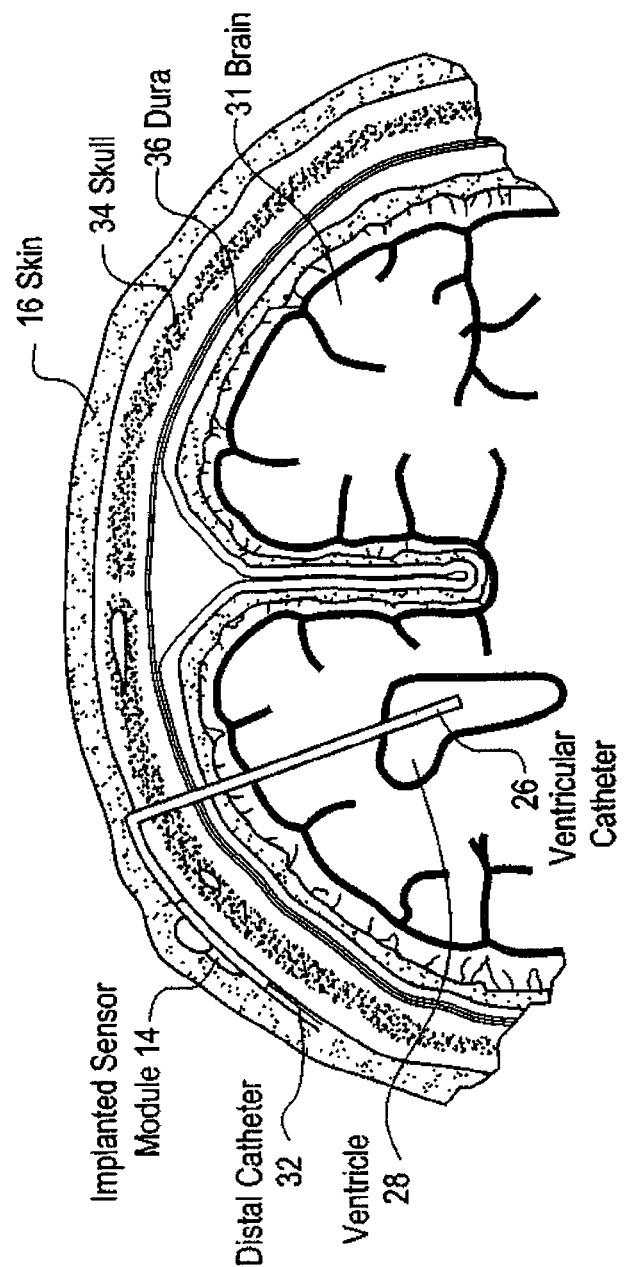
FIG. 2 is simplified coronal cross sectional diagram illustrating how the sensor module may be implanted in a typical use with a patient.

A typical in vivo implementation is shown in the simplified longitudinal cross-sectional diagram of FIG. 2. A hollow ventricular catheter 26 is placed surgically into a cerebrospinal fluid (CSF) filled ventricle 28 of the brain 31. The CSF is communicated via the ventricular catheter 26 to the implant 14. The physiological parameter 12, intracranial pressure, is sensed and transmitted via NIR telemetry signal 18 from the implant 14, to the external coupling module 20, through the overlying skin 16. In the scenario of a ventriculoperitoneal shunt, the CSF exits the implant 14 and passes, via a distal catheter 32, through a valve assembly (not shown) and ultimately to the peritoneal cavity of the abdomen (not shown). The implant 14 is installed superficial to, or embedded within, the skull 34. Dura 36 is depicted as an additional anatomical landmark.

Choice of the preferred NIR wavelength for transcutaneous telemetry pursuant to the present invention is dependent upon the absorption coefficients of the intervening tissues. The absorption by melanosomes dominates over the visible and near-infrared spectra to about 1100 nm, above which free water begins to dominate. Absorption by the dermis decreases monotonically over the 700-1000 nm range. Whole blood has a minimum absorption at about 700 nm but remains low over the 700-1000 nm range. The nadir in the composite absorption spectrum therefore lies in the 800-1000 nm range.

The actual wavelength utilized is therefore dictated by the optimal spectral range (as above) and the availability of suitable semiconductor emitters. Several suitable wavelengths may include, but are not limited to: 760 nm, 765 nm, 780 nm, 785 nm, 790 nm, 800 nm, 805 nm, 808 nm, 810 nm, 820 nm, 830 nm, 840 nm, 850 nm, 870 nm, 880 nm, 900 nm, 904 nm, 905 nm, 915 nm, 920 nm, 940 nm, 950 nm, 970 nm, and 980 nm. Wavelengths outside this range may be used but will be subject to greater attenuation by the intervening tissues.

Figure 3A:
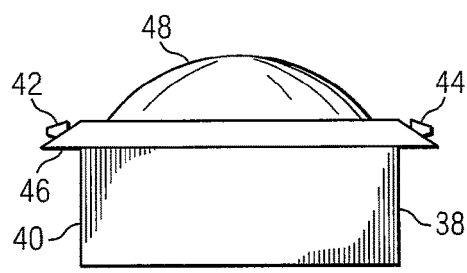
FIG. 3a is a simplified side elevational view of an implanted sensor module in accordance with the invention.
Figure 3B:
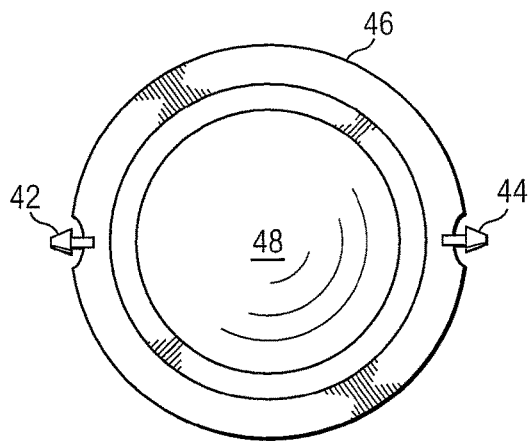

Various designs for the implant 14 housing are suitable and a representative design is depicted in FIG. 3a and FIG. 3b which respectively depict simplified side elevational and top plan views of the device 38. Device 38 includes a cylindrical external housing 40 having a fluid inlet port 42 and fluid outlet port 44 for cerebral spinal fluid (CSF). The external housing 40 must be biocompatible, rigid, and have a superficial face which is substantially transparent to NIR telemetry signal 18. A material such as polycarbonate (optically transparent to near infrared wavelengths) may be used.

The footprint of the implant in the preferred embodiment is round to accommodate the implant's power supply coil. Furthermore, a round footprint allows the external housing 40 to be easily recessed into the skull 34 during implantation using a twist-drill. The seating flange 46 limits the depth of the recess such that the seating flange 46 remains flush with the skull 34 surface.

One preferred embodiment may include a reservoir access dome 48, or "Rickham reservoir," which is an integrated self-sealing chamber made of a material such as Silastic. A needle may be introduced percutaneously through the skin 16 into the reservoir access dome 48 to allow access to cerebrospinal fluid within the implant 14, which in turn, communicates with cerebrospinal fluid within the brain ventricle 28 via fluid inlet port 42 and ventricular catheter 26. Alternate embodiments of the external housing 40 may include alternative locations for the fluid ports, such as placement of the fluid inlet port 42 on the bottom of external housing 40.

Figure 4:
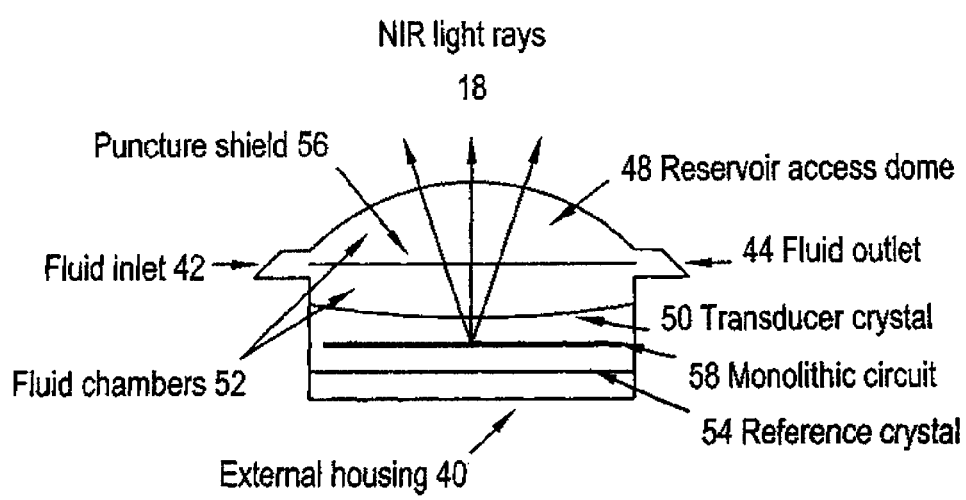
FIG. 4 is a schematic longitudinal cross sectional view of the implanted sensor module.

A schematic longitudinal cross sectional view of the implant 14 appears in FIG. 4. Cerebrospinal fluid enters fluid chambers 52 via fluid inlet 42. A transducer crystal 50 is mounted across external housing 40 to act as a diaphragm in contact with fluid chamber 52. In the preferred embodiment, the transducer crystal 50 is a quartz (silicon dioxide) crystal which exhibits a change in oscillation frequency as a predictably stable function of deformation, and hence pressure, on transducer crystal 50. In FIG. 4 the transducer crystal 50 is depicted in the deformed state. The transducer crystal 50 may be composed of a biocompatible material (e.g., silicon dioxide) which will not significantly degrade in mechanical properties over the lifetime of the implant. Important characteristics of the sensor to be employed are sensitivity, electromechanical stability, absolute pressure accuracy, biocompatibility and electrical noise immunity. The quartz crystal transducer crystal 50 may be trimmed at the factory during fabrication to achieve calibration.

A reference crystal 54 is also housed within the implant 14. This reference crystal 54 is of identical construction to that of transducer crystal 50 and the difference in oscillation frequency between these crystals correlates directly with the deformation, and hence, pressure applied to the transducer crystal 50.

A monolithic circuit 58 within the implant 14 contains the necessary electronics to operate the implanted sensor module. These electronics act to modulate the output of a near-infrared emitter as a function of pressure on the transducer crystal 50.

A puncture shield 56 serves to protect transducer crystal 50 from damage due to needles introduced through the reservoir access dome 48. The puncture shield 56 as well as the transducer crystal 50 are substantially transparent to the NIR telemetry signal 18.

Transcutaneous telemetry from the implant 14 is transmitted optically to the external coupling module 20 via NIR telemetry signal 18. In vivo, soft tissues are relatively permeable to wavelengths within the near infrared (NIR) spectrum. This permeability, coupled with specific hemoglobin absorption peaks, is exploited in non-invasive transcutaneous oxygenation monitors and NIR spectroscopy. In these applications it is the relative absorption at specific wavelengths that is capitalized upon, rather than the transmission of data over a tissue-permeable wavelength as in the present invention.

Analog signal transmission is not suitable due to the unpredictability of the NIR absorption by the skin 16. However, any one of numerous methods for digital signal transmission may be incorporated. Existing serial data transmission protocols, whether synchronous or asynchronous, require complex electronics to encode the data. More simply, frequency modulation or pulse-width modulation may be employed, particularly since the bandwidth of the physiological data is low. In the preferred embodiment, frequency modulation is used.

A computer within the processing and display module 24 calculates the physiological parameter 12 from the NIR telemetry signal 18, as detected by external coupling module 20, and represents these data either in numerical, graphical, or analog format.

One preferred embodiment of the invention employs a pressure transducer crystal 50 composed of an x-cut quartz crystal. In typical transducer applications, mechanical deformations of a crystal are detected as piezoelectric charges developed across the face of the crystal. While this works well for time-varying signals, leakage currents render this technique inapplicable to measurement of static or slowly-changing deformations of a crystal.

An alternate approach is to resonate an x-cut crystal at its fundamental frequency; mechanical deformation of the crystal, such as due to an applied pressure, will alter the resonant frequency in a predictable fashion. The pressure applied to the crystal face is thus calculated by measuring the change in crystal oscillation frequency. This technique is applicable to both static and dynamic measurements and is extremely stable as a function of time.

The sensitivity of a crystal acting as a pressure-sensitive diaphragm is dependent upon its stiffness and mounting configuration. To achieve maximal sensitivity, the crystal should be as thin as possible, yet adequately robust to withstand the pressure requirements of the application without exceeding the crystal's burst pressure.

The pressure transducer crystal 50 is in contact with cerebrospinal fluid within the fluid chamber 52. The chemical composition of quartz (silicon dioxide) has been demonstrated to be biocompatible and have minimal biofouling. Biofouling is further minimized by surface polishing of the crystal surface during manufacturing. Long-term resonant frequency stability is theoretically ensured despite biofouling due to the flexural stiffness of the crystal being orders of magnitude greater than that of surface contaminant proteins.

Figure 5A:
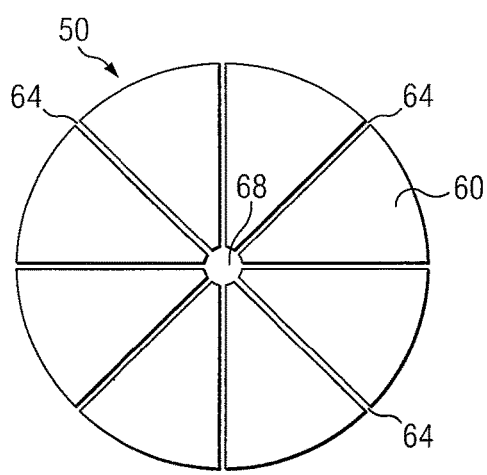
FIG. 5a is a plan view of the upper side of a crystal which may be used in one embodiment of the present invention.
Figure 5B:
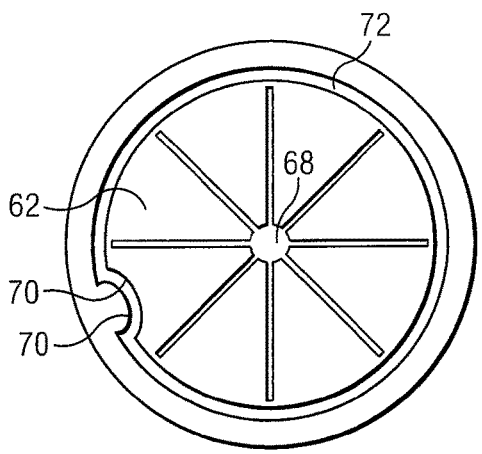

In one preferred embodiment, a gold (Au) coaxial electrode pattern is deposited onto the crystal as shown in FIGS. 5a and 5b, which are respectively top 60 and bottom 62 plan views of the crystal. The top side is the biofluid side; the bottom-side 62 is where electrical contact is made. Gold has also been demonstrated to be biocompatible and have minimal biofouling. By lapping gold around the edge from the top 60 to the undersurface at bottom 62 of the crystal, the surface at 60 in contact with the cerebrospinal fluid can be made entirely referenced at ground potential. No electrical connections 70 are in contact with the CSF as electrodes from each face of the crystal are available on the undersurface 62 of the crystal and are separated by an inter-electrode gap 72. Slots 64 may be etched in the gold electrode surface to reduce or eliminate eddy currents from forming, hence improving power coupling from the external coupling module 20 to the implant 14. Additionally, an IR transmission port 68 may be left without metallization to allow transmission of infrared light through the crystal.

Pressure on the transducer crystal 50 will cause the oscillation frequency to decrease. Consequently, to ensure a monotonic increase in differential frequency with increasing pressure, it is necessary for nominally identical transducer crystal 50 and reference crystal 54 to be matched such that the transducer crystal 50 has the lower natural frequency of the pair. Alternatively, the transducer crystal 50 may be designed to be nominally lower in frequency than the reference crystal 54 to increase the temporal resolution of the system, but at the expense of immunity to frequency drift.

Figure 6:
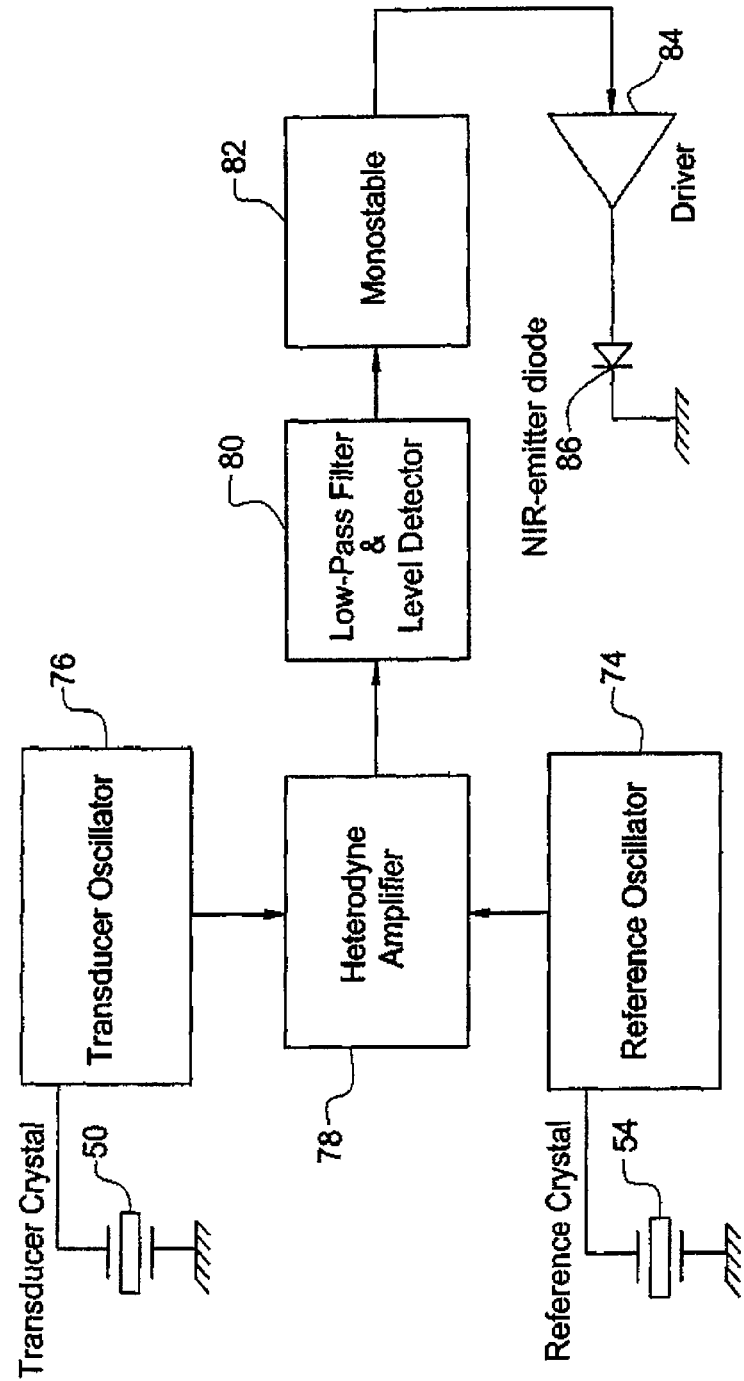
FIG. 6 is a schematic electrical block diagram illustrating a preferred arrangement for measuring a patient pressure parameter in accordance with the invention.

In the preferred embodiment, the sensitivity and long-term stability of the system is maximized using a frequency-coherent detection scheme. As shown in FIG. 6, two identical, yet independent, crystal oscillators are employed. A reference crystal 54 serves a reference oscillator 74 while the transducer crystal 50 serves the transducer oscillator 76. The difference in frequency between the two oscillators is detected using a heterodyne amplifier 78. The difference frequency is ultimately measured and used to compute the pressure applied to the transducer crystal 50. The inherent long-term stability of the quartz crystal-controlled transducer oscillator 76 is augmented by cancellation of drift (thermal, aging, parasitic capacitance, etc.) by the reference oscillator 74.

The output of the heterodyne amplifier 78 is low-pass filtered to obtain the beat-frequency and a level detector 80 with hysteresis is used to derive a digital signal to trigger a monostable multivibrator 82 at the beat frequency. The output of the monostable multivibrator 82 is used to modulate the NIR-emitter diode 86 via driver 84. The output pulse of the monostable multivibrator 82 is selected to be as short as feasible to minimize the power consumption of the implant. The system is designed such that lower, more physiological pressures, are associated with lower beat frequencies, again to decrease current consumption. As intracranial pressure rises, the beat frequency increases. The dynamic range of the frequency change is determined by the electromechanical characteristics of the transducer crystal 50 over the operating pressure range. A two-point calibration of the implant 14 may be performed at the factory by trimming of the components on the monolithic circuit 58. The minimum on-time pulse width for the NIR-emitter diode 86 is typically limited by the bandwidth of the detector electronics in the external coupling module 20.

Various semiconductor materials are known which are capable of emitting suitable NIR wavelengths. In practice, most are light-emitting diodes (LEDs). The light output intensity is generally proportional to the diode's forward current, and depending on the device, this current can typically range from 20 mA to 1.5 A. Laser diodes tend to have greater optical output but at the expense of higher current requirements and more complicated driver circuitry. High current requirements are not feasible in a miniature implanted device which relies on transcutaneously derived power.

The Vertical Cavity Surface Emitting Laser (VCSEL) provides a high-performance, low-current, high-optical-power solution. In the preferred embodiment, a VCSEL is employed as the NIR-emitter diode 86, such as a Honeywell SV5637 VCSEL laser diode which produces an 850 nm 1.25 mW/cm output at a mere 10 mA forward current. Furthermore, with the vertical cavity design, the light beam radiates perpendicular to the wafer surface. This facilitates the fabrication of the laser diode and the remainder of the implant 14 electronics on a microminiaturized monolithic circuit 58.

Figure 7:
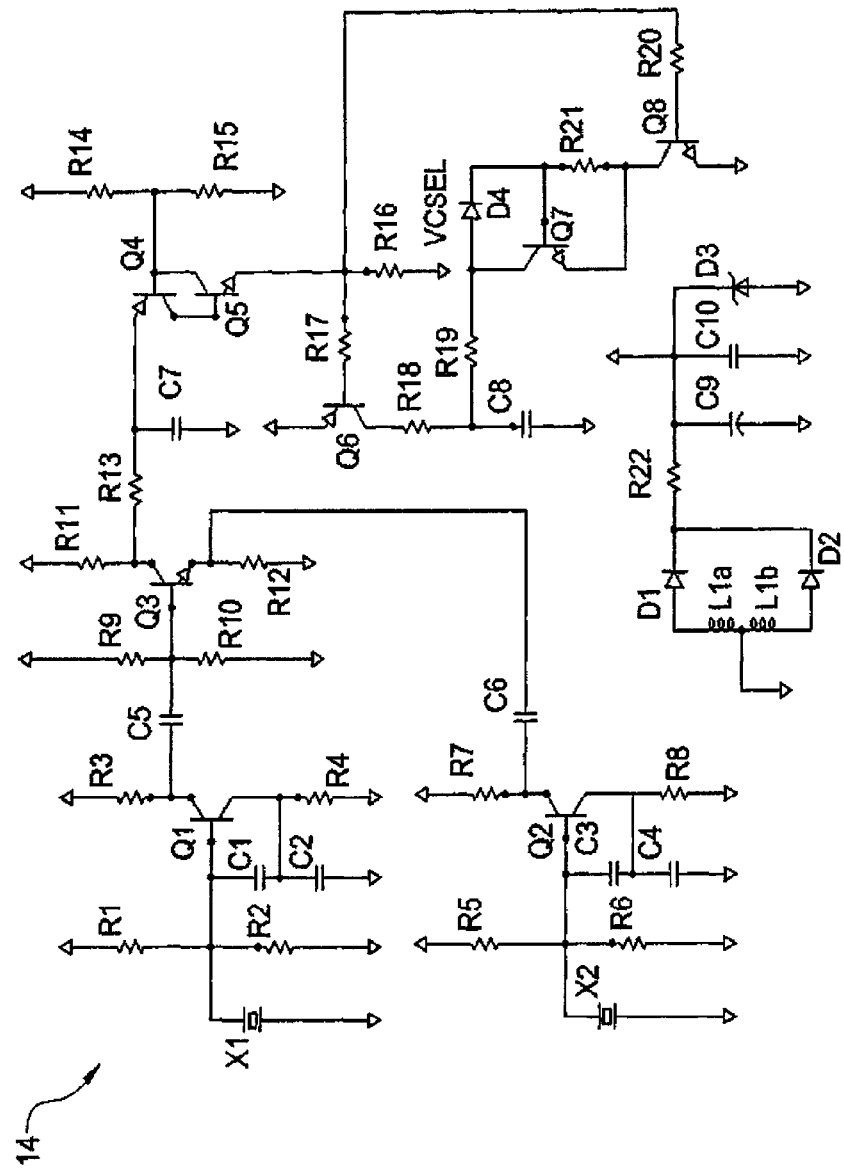
FIG. 7 is an electrical schematic diagram depicting further details of the arrangement shown in FIG. 6.

FIG. 7 depicts a preferred embodiment of the implant 14 circuitry. Referring also to FIG. 6, transistors Q1 and Q2 compose two identical Colpitts crystal oscillators, 76 and 74, respectively. X1 is the transducer crystal 50 of FIG. 6 while X2 is the reference crystal 54. X1 and X2 may have the same nominal resonant frequency or may be deliberately tuned with a small offset. Due to these oscillators being essentially identical, the long-term drift, thermal drift, and voltage dependence cancels.

The outputs of each oscillator 76 and 74 are ac-coupled via capacitors C5 and C6 to a heterodyne amplifier 78 (FIG. 6) composed of Q3. The low-pass filtered (R13 and C7) heterodyne signal has a fundamental frequency equal to the frequency difference between the two oscillators 76 and 74. The heterodyne signal is dc-coupled to Q4 and Q5 which are configured as a programmable unijunction-transistor voltage comparator and this serves as a level detector 80. The set-point of the comparator is determined by the voltage divider composed of R14 and R15.

The output of the unijunction transistor pair provides a digital signal which turns the NIR emitter diode 86, laser diode D4, on and off at the difference frequency of the two oscillators. A monostable multivibrator 82 (FIG. 6) is composed of Q6, Q8, C8 and associated resistors. When the input voltage is below the unijunction set-point, transistor Q6 conducts, allowing capacitor C8 to charge through resistor R18. The value of C8 is selected to provide adequate charge to drive laser diode D4 at the desired forward current for a nominal minimum period. R18 is selected to provide adequate charging current during one cycle while minimizing current drain on the power supply. Peak laser diode forward current is regulated by Q7. When the voltage-comparator input exceeds the threshold voltage, Q6 turns off to isolate the current drain of the laser diode from the supply rail, while Q8 conducts current from C8 to the laser diode D4. The duration that the laser remains on is determined by the values of C8, R19, and the minimum forward lasing current of D4. Current consumption is minimized by keeping the duty cycle of the laser diode low.

Power to the implant 14 is inductively coupled to coil LI via a time-varying electromagnetic field 22 (FIG. 1) which is applied transcutaneously by the complementary external coupling module 20. Coil LI may be a wire wound as a 'short solenoid' which is embedded in the implant's external housing 40 (FIG. 3*a*), or as in a preferred embodiment, a photochemically-etched metallic spiral on a suitable substrate such as the monolithic circuit 58 (FIG. 4). The induced electromotive force from center-tapped coil LI is then rectified by diodes D1 and D2, which are ideally of the Schotkey type. This produces a direct current (DC) which is subsequently low-pass filtered by resistor R22 and capacitors C9 and C10 to derive a DC supply voltage. A zener diode D3 across the output is used to suppress voltage transients which might be induced by extraneous magnetic fields, such as from a Magnetic Resonance Imaging (MRI) scanner.

Figure 8:
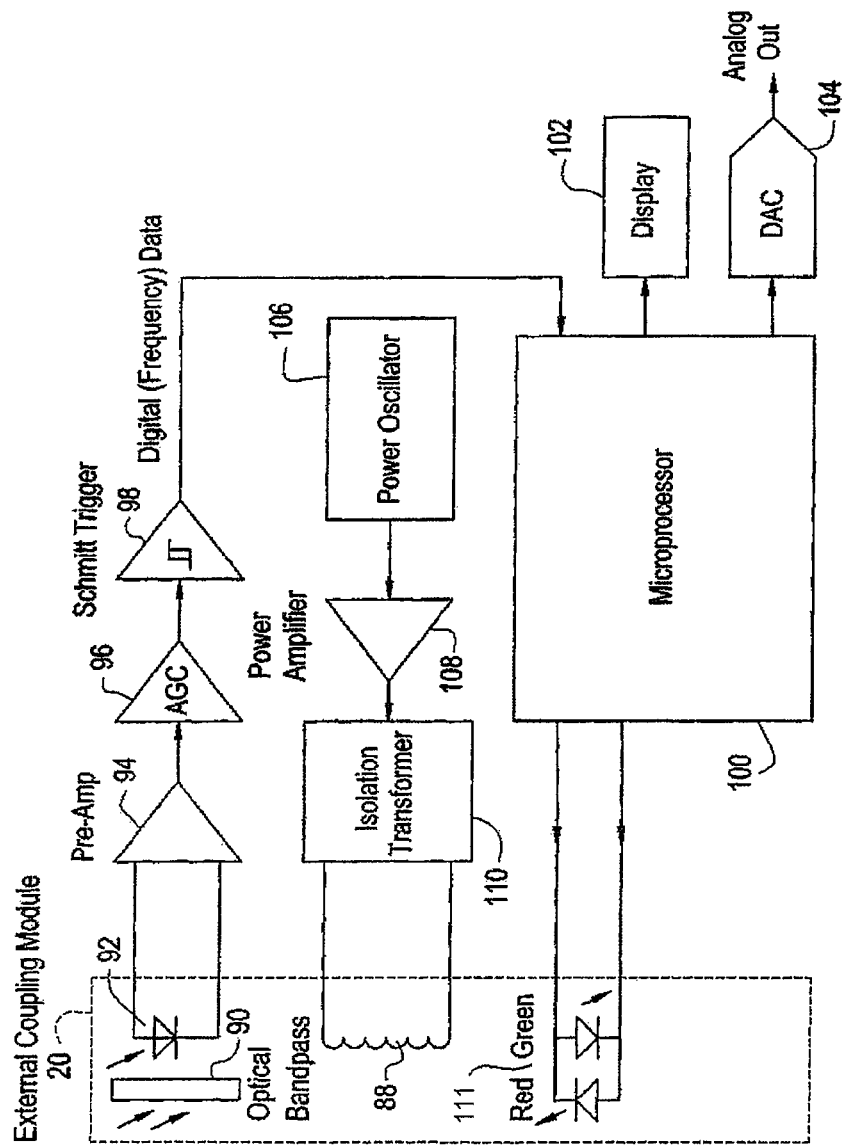
FIG. 8 is a schematic block diagram of the electronics used in the system of the invention which are external to the patient.

Most of the external electronics may be conveniently located in a housing mounted at the bedside of the patient. FIG. 8 depicts a schematic block diagram of the electronics external to the patient. An external coupling module 20 houses electronic components which are necessarily closely associated with the implant 14. A single cable (not shown) goes from the external coupling module 20 to the processing and display module 24. This cable is shielded to minimize spurious electromagnetic radiation emission. The external coupling module 20 is placed in proximity to, i.e., over, the implant 14 to telemeter the physiological parameter 12. The external coupling module 20 may be disc-shaped and contains a coil 88 to deliver inductively-coupled power to the implant 14. An optical bandpass filter 90 on the undersurface of the external coupling module 20 permits NIR telemetry signal 18 (FIG. 1) to reach a semiconductor photodetector 92. In a preferred embodiment, a photodiode is used. Ideally, this device is matched with the NIR emitter diode 86 such that the peak wavelength sensitivity of photodetector 92 corresponds to that of the NIR emitter diode 86. Optical signal-to-noise ratio (SNR) is improved using a narrow optical bandpass filter 90. Further improvements in SNR may be achieved through biasing of the photodiode. Advanced techniques such as phase-coherent or frequency-coherent detection may be employed.

The external coupling module 20 may optionally contain a preamplifier 94 for the photodetector 92. The photodetector 92 signal is further conditioned by an automatic gain control (AGC) amplifier 96. In the preferred embodiment, an edge-detector such as a Schmitt trigger 98 is used to detect the rise and fall of the photodetector 92 output, which in turn correlates with NIR emitter 86 pulse frequency. A microprocessor 100 converts the pulse frequency to a pressure value based on known calibration constants. The microprocessor 100 may then perform any additional signal processing prior to outputting the pressure data either graphically, numerically on a visual display 102, or in analog fashion via digital-to-analog converter 104. A calibrated analog output facilitates connection to existing patient-care monitoring equipment.

A high-frequency oscillator 106 and associated power amplifier 108 provide the necessary drive current to coil 88 to produce the time-varying magnetic flux 22 (FIG. 1) to power the implant 14. Isolation transformer 110 provides galvanic isolation between the processing and display module 24 and the patient-connected external coupling module 20.

A visible bi-colored LED 111 mounted on the external coupling module 20 (FIG. 1) casing aids in the positioning of the external coupling module over the implant 14. The LED indicates red when power is applied to external coupling module 20 and indicates green when NIR telemetry signal 18 (FIG. 1) is detected from the implant 14. Thus, the green LED may be used to aid in positioning of the external coupling module 20 over the implanted sensor module as the NIR emitter diode 86 (FIG. 6) will only be detected when there is adequate proximity and collinear alignment of the coil 88 and secondary (LI of FIG. 7) coils. The outer casing of external coupling module 20 is optically opaque at the NIR emitter diode 86 wavelength to avoid exposure of medical personnel to the optical radiation. The external coupling module 20 may be held in place by any convenient means, such as with a headband, a stocking cap, or preferably by an articulated arm attached to the bedside.

Each pressure transducer system, e.g., transducer 50 and reference 54 crystal pair, (FIG. 4) is factory calibrated using a two-point calibration. The difference frequency at zero gauge pressure is used as a baseline and the difference frequency at a specified physiological extreme, e.g., 100 mmHg, is used to compute the slope of the two-point calibration. These data are then sufficient to compute the actual transducer pressure with high linearity and monotonicity given that the transducer crystal 50 frequency is intrinsically lower than the reference crystal 54 frequency.

The calibration coefficients obtained in the above fashion may be stored electronically in a database accessible from the internet. Upon initialization of the pressure recordings from the transducer, the database may be accessed and the proper calibration coefficients entered into the processing and display module 24. The database may be indexed by patient identifier.

The VCSEL laser diodes considered for use as the NIR emitter provide a power output of 5 mW or less. The amount of energy absorbed by the overlying tissue would be well below the safety standard of 90 mW. Furthermore, the design described inherently has a 'safety interlock' as power is only applied to the implanted sensor module when the external coupling module is held directly over the implant 14. The NIR-opaque external coupling module 20 prevents an observer from gazing into the laser beam emanating from the implant. A visible light photo detector may be embedded in the patient-side of the external coupling module 20 to prevent the device from being energized when ambient light is present. This necessitates that the external coupling module be applied to the scalp overlying the implant 14 (FIG. 1) prior to telemetry commencing.

The preferred embodiment described in the foregoing provides a simple and practical means for unidirectional transcutaneous telemetry of a physiological parameter using near infrared light. However, the direction of information travel is immaterial. If both the intracorporeal and extracorporeal devices are equipped with a transceiver (i.e., emitter and detector), then data may flow in bidirectional fashion.

Two different wavelengths of infrared light may be utilized to minimize "crosstalk" during communication between the intra- and extra-corporeal devices. The choice of transmission wavelength is dependent upon the permeability of the tissue at that wavelength and the electrical characteristics of the semiconductor emitter. Appropriate choices could include, but are not limited to, 850 nm and 1050 nm. Because biological tissues tend to scatter incident light in unpredictable fashion, it is conceivable that light from an emitter in either device could be reflected back upon the receiver in that same device. By specifying a particular wavelength for transmission in a given direction, the receivers may be equipped with narrow band-pass filters to selectively respond only to incident light from the intended sender. Furthermore, incorporation of such band-pass filters gives the desired effect of excluding ambient light which could adversely affect the signal-to-noise ratio of the communication pathway.

Existing electronic implant devices typically utilize radio frequency (RF) telemetry during application of a strong magnetic field (to actuate a reed switch); narrow bandwidth optical telemetry would markedly reduce or eliminate the susceptibility of these devices to the electromagnetic fields experienced during Magnetic Resonance Imaging.

In an alternative embodiment, the functionality of the implant is maximized by incorporating a microprocessor into the implanted device. While increasing device complexity, it allows for complex data transmission schemes, signal processing within the device, storage and modification of calibration data, and a broader information transmission bandwidth.

Also, the NIR emitter may serve a dual role. Physiological pressures, such as that of cerebrospinal fluid, may be measured using the same infrared emitter as used for the transcutaneous telemetry of data. An optical means of pressure measurement could involve the use of a reflective strip on a distensible membrane which is in contact with the cerebrospinal fluid. The displacement of the membrane is considered a function of pressure. Hence, by measuring the degree of displacement at a given location on the membrane, the applied pressure may be calculated. A portion of the light emitted by the incorporated NIR emitter is bounced off the reflective area of the membrane and the resultant reflection pattern is detected by a linear array of photo detectors such as a charge-coupled device. Alternatively, a diffraction grating may be utilized and the resultant interference pattern analyzed.

The inclusion of a semiconductor temperature sensor within the implant electronics would allow temperature compensation for variations in ambient temperature. This is particularly important with optical pressure transduction schemes utilizing diffraction pattern analysis due to the high sensitivity of such systems to dimensional changes from thermal expansion.

The transcutaneous telemetry of data via infrared light beam serves as the basis for a plethora of applications. This technology may serve as a replacement for existing radio frequency (RF) telemetry systems (incorporated in cardiac pacemakers and neurostimulators) which may be affected by environmental RF energy such as present in MRI scanners.

Furthermore, complex serial data transmission protocols are facilitated by the high bandwidth, allowing many physiological parameters to be transduced simultaneously in real-time.

A logical extension of the technology described herein is incorporation of a photometric system for measuring brain tissue oxygenation. The techniques for spectrophotometric measurement of total hemoglobin, oxyhemoglobin, and deoxyhemoglobin are described in the literature. In summary, tissue absorption at several near infrared wavelengths (e.g., 780 nm, 805 nm, 830 nm) is used to compute the concentration of each chromophore.

Figure 9:
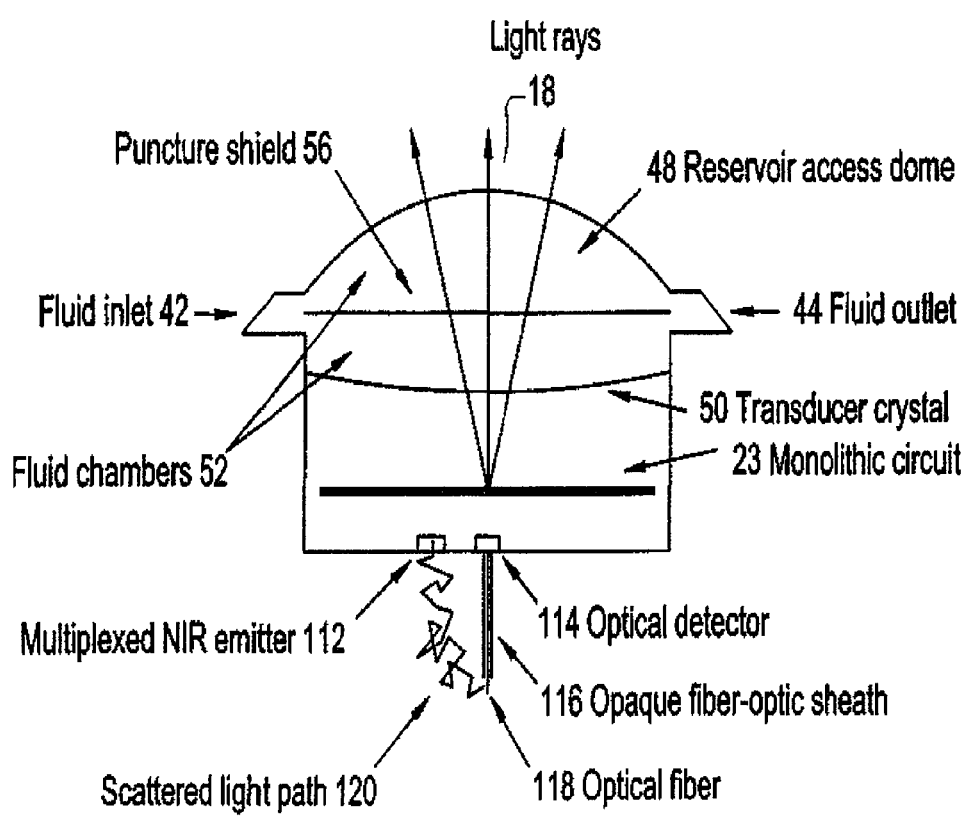
FIG. 9 is a schematic longitudinal cross-section illustrating a sensing device for an embodiment of the invention which is suitable for monitoring brain tissue oxygenation.

An illustrative system for implementing ICP and brain tissue oxygenation monitoring is depicted in FIG. 9. Portions of the implant which are identical to that in FIG. 4 are identified by the same reference numeral. In this system, a microprocessor is used within the implanted device to perform data analysis and facilitate bidirectional transcutaneous NIR communication. Separate wavelengths are used for each of the communication send and receive channels.

In FIG. 9, a brain oxygenation sensor is comprised of NIR emitters 112 of the appropriate wavelengths (e.g., 780 nm, 805 nm, 830 nm) which are oriented such that their light beams are directed downward through NIR-transparent windows in the base of the implant housing. Power consumption by the NIR emitters 112 is minimized through multiplexing; briefly turning on each emitter sequentially at a rate fast enough to make the physiological parameter 12 of interest relatively quasistatic. A fiber optic catheter 118 extends from the implant housing into the brain tissue and conveys transmitted NIR light 120 from the multiplexed NIR-emitters 112 back to an optical detector 114 to measure optical absorbance. An optically opaque sheath 116 covers all but a small portion of the tip of the fiber optic catheter 118 such that the light must travel a minimum known distance through the brain tissue. Simultaneous linear equations available in the literature relate the relative absorbance of light at each wavelength to spectrophotometrically calculate the concentration of total hemoglobin, oxyhemoglobin and deoxyhemoglobin. These calculations may be performed by a microprocessor embedded into the implanted device. The microprocessor device also manages asynchronous serial data communications with the extracorporeal monitor via a bidirectional dual-wavelength NIR telemetry signal 18 providing handshaking, sending of the chromophore and ICP readings, and receiving of calibration constants.

Figure 10A:
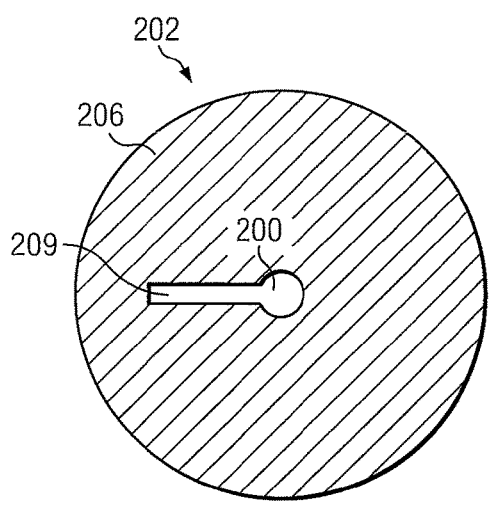
FIG. 10a is a plan view of the upper side of a crystal which may be used in the implant module of the present invention.
Figure 10B:
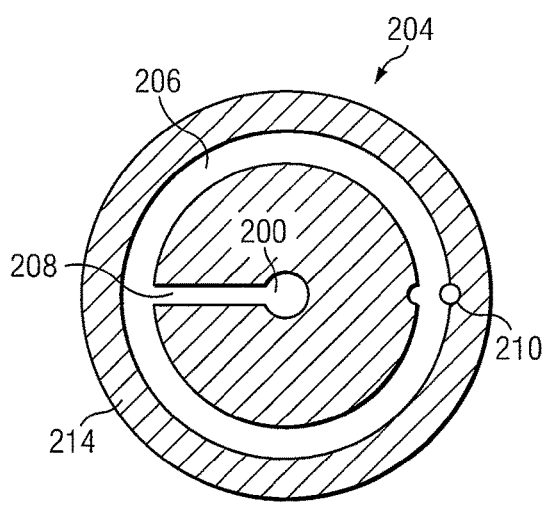
FIG. 10b is a plan view of the lower side of a crystal which may be used in the implant module of the present invention.

In another preferred embodiment, a gold (Au) coaxial electrode pattern is deposited onto the crystal as shown in FIG. 10a and FIG. 10b, which are respectively top 202 and bottom 204 plan views of the crystal. Top side 202 is the biofluid side; bottom-side 204 is where electrical contact is made. Gold has also been demonstrated to be biocompatible and have minimal biofouling. By lapping gold around the edge from the top 202 to the undersurface at bottom 204 of the crystal (shown as 214), the surface at 202 in contact with the cerebrospinal fluid can be made entirely referenced at ground potential. No electrical connections 210 are in contact with the CSF as electrodes from each face of the crystal are available on the undersurface 204 of the crystal and are separated by an inter-electrode gap 206. A single slot 208 is etched in the gold electrode surface of bottom 204 and a slot 209 is etched in top 202 in order to reduce or eliminate eddy currents from forming and hence improving power coupling from the external coupling module 20 to the implanted sensor module 14. Additionally, an IR transmission port 200 may be left without metallization to allow transmission of infrared light through the crystal.

A cross-section of a preferred embodiment of the ICP transducer implant is shown in FIG. 11. A generally cylindrical stainless steel housing 302 is provided which is gold flashed. Housing 302 includes threaded opening 331 and threaded opening 309. Housing 302 further includes seating ring 318, seating ring 316 and seating ring 314. Each seating ring, respectively, is machined into the inside of the housing and is comprised of a generally annular ledge for support of the internal components of the implant. Transducer crystal 304 is seated adjacent seating ring 318 and held in place by circumferential fillet 354. Circumferential fillet 354 is a gold fillet and attaches to both the transducer crystal and seating ring 318 to firmly form a mechanical bond between transducer crystal 304 and housing 302. Integrated monolithic circuit 308 fits within seating ring 316 and is held in place by circumferential fillet 352. Circumferential fillet 352 is gold and forms a mechanical bond between integrated monolithic circuit 308 and housing 302.

Reference crystal 306 is seated within seating ring 314 and held in place by circumferential fillet 350. Circumferential fillet 350 is also gold.

Housing closure 399 is a gold flash stainless steel disk which includes annular threads. Housing closure 399 is threaded into threaded opening 309 in housing 302 and forms a hermetical seal to the interior of housing 302.

FIGS. 11 and 12 show an alternative embodiment of the ICP transducer implant 1100. Housing cap 330 is a generally cylindrical structure comprised of seating ring 339, threaded exterior 340 fluid inlets 332, fluid outlet 333 and optical opening 342. A silastic dome 335 is fixed on the exterior surface 336 of housing cap 330. Silastic dome 335 is fixed to exterior surface 336 with a silastic RTV compound. Fluid inlet 332 and fluid outlet 333 are generally rectangular ports machined in a radial fashion in exterior surface 336. Fluid inlet 332 and fluid outlet 333 are in ducted communication with interior chamber 337. Silastic dome 335 is a NIR transparent flexible material capable of penetration by needles for extraction of fluid from internal chamber 337 when the transducer implant is in use. Shield 341 is fitted within seating ring 339 and held in place by circumferential fillet 338. Shield 341 is an IR transparent material capable of withstanding needle sticks without penetration. Threaded exterior 340 is threaded into threaded opening 331, affixing housing cap 330 adjacent transducer crystal 304. Shield 341 includes holes 349 around its perimeter which provide ducted communication between interior chamber 337 and the top surface of transducer crystal 304.

Transducer crystal 304 is held in electrical connection with integrated monolithic circuit 308 through connector 312. Reference crystal 306 is held in electrical connection with integrated monolithic circuit 308 through connector 310. Integrated monolithic circuit 308 is provided with infrared LED 320. Infrared LED 320 is positioned directly beneath transducer crystal 304 in a position to emit radiation through transducer crystal 304, shield 341, and silastic dome 335, toward the exterior of the implant for reception and decoding of infrared signals.

Referring to FIG. 13a, an alternate embodiment of the ICP transducer implant is shown at 1300. In this embodiment, a stainless steel housing 302 is provided. The stainless steel housing is gold flashed for bioinertness. In this embodiment, seating ring 376 is provided on the interior of housing 302. Adjacent seating ring 376 is sealed cylindrical enclosure 370. Transducer crystal 305 is seated adjacent a seating ring and held in place by a circumferential fillet.

Referring then to FIG. 13b, sealed cylindrical enclosure 370 includes seating ring 394 and threaded opening 391. Upper fixed pressure chamber 393 and lower fixed pressure chamber 395 are provided connected by longitudinal channel ducts 392. Reference crystal 371 is placed within upper fixed pressure chamber 393 and adjacent seating ring 394. Reference crystal 371 is held in place by annular fillet 397. Channel ducts 392 surround the circumference of reference crystal 371 and provided ducted communication between upper fixed pressure chamber 393 and lower fixed pressure chamber 395. An electrical connector 396 is provided on reference crystal 371. Enclosure cap 390 is a cylindrical disk having annular threads. Enclosure cap 390 is threaded into threaded opening 391 in sealed cylindrical enclosure 370. External electrical connection is provided to reference crystal 371 via electrical connector 396 and external connector 398 in enclosure cap 390.

Referring to FIG. 13a, sealed cylindrical enclosure 370 is seated adjacent seating ring 376 and held in place by circumferential fillet 377. In the preferred embodiment, housing closure 399 is in direct mechanical contact with sealed cylindrical enclosure 370 pressing it firmly against seating ring 376. External connector 398 provides electrical connection with connector 311 in direct electrical contact with integrated monolithic circuit 308.

In this preferred embodiment, the sealed cylindrical enclosure is provided to isolate reference crystal 371 from the interior of housing 302 to avoid any potential deflection from the fluid pressure in internal chamber 337. The pressure in internal chamber 337 enclosure is atmospheric. In other embodiments the internal chamber is evacuated during manufacture providing a pressure of as close to zero psi as possible.

In yet another preferred embodiment of transcutaneous monitoring of ICP, a quiescent sensor is employed in combination with a radio frequency identification (RF-ID) tagging device in the subcutaneous implant. Such a subcutaneous implant 14 and corresponding external coupling module 20 is shown in the block diagram of FIG. 14, where the implant 14 is placed under skin 16, the external coupling module 20 is brought over skin 16 and in the vicinity of implant 14, and the external coupling module 20 percutaneously reads the parameter of interest, intracranial CSF pressure.

The implant 14 comprises two high Q tuned resonant circuits, sensor circuit 520 for sensing pressure and reference circuit 530, and an RF-ID tagging device 542 for storing information. The resonant frequency of sensor circuit 520 is $f_1$ and the resonant frequency of reference circuit 530 is $f_0$. When excited by external time-varying electromagnetic fields, resonantly tuned sensor circuit 520 and resonantly tuned reference circuit 530 will tend to oscillate at their respective resonant frequencies, $f_1$ and $f_0$, with a very narrow function of frequency, typical of high Q frequency resonances. Tuned sensor circuit 520 is comprised of sensor crystal 521 connected in series with inductive coil 525. Sensor crystal 521 is in physical contact with a biological environment (intracranial CSF) and experiences pressure and temperature equilibrium with that environment. Tuned reference circuit 530 is comprised of reference crystal 531 connected in series with inductive coil 535. Reference crystal 531 is pressure sealed from given biological environment and held at a fixed pressure $P_0$ (e.g., normal atmospheric pressure) while maintaining temperature equilibrium with given biological environment.

Inductive coil 525 and inductive coil 535 have 10 turns and 5 mm diameter and are constructed with 27 AWG bondable polymer insulated copper wire.

Figure 18:
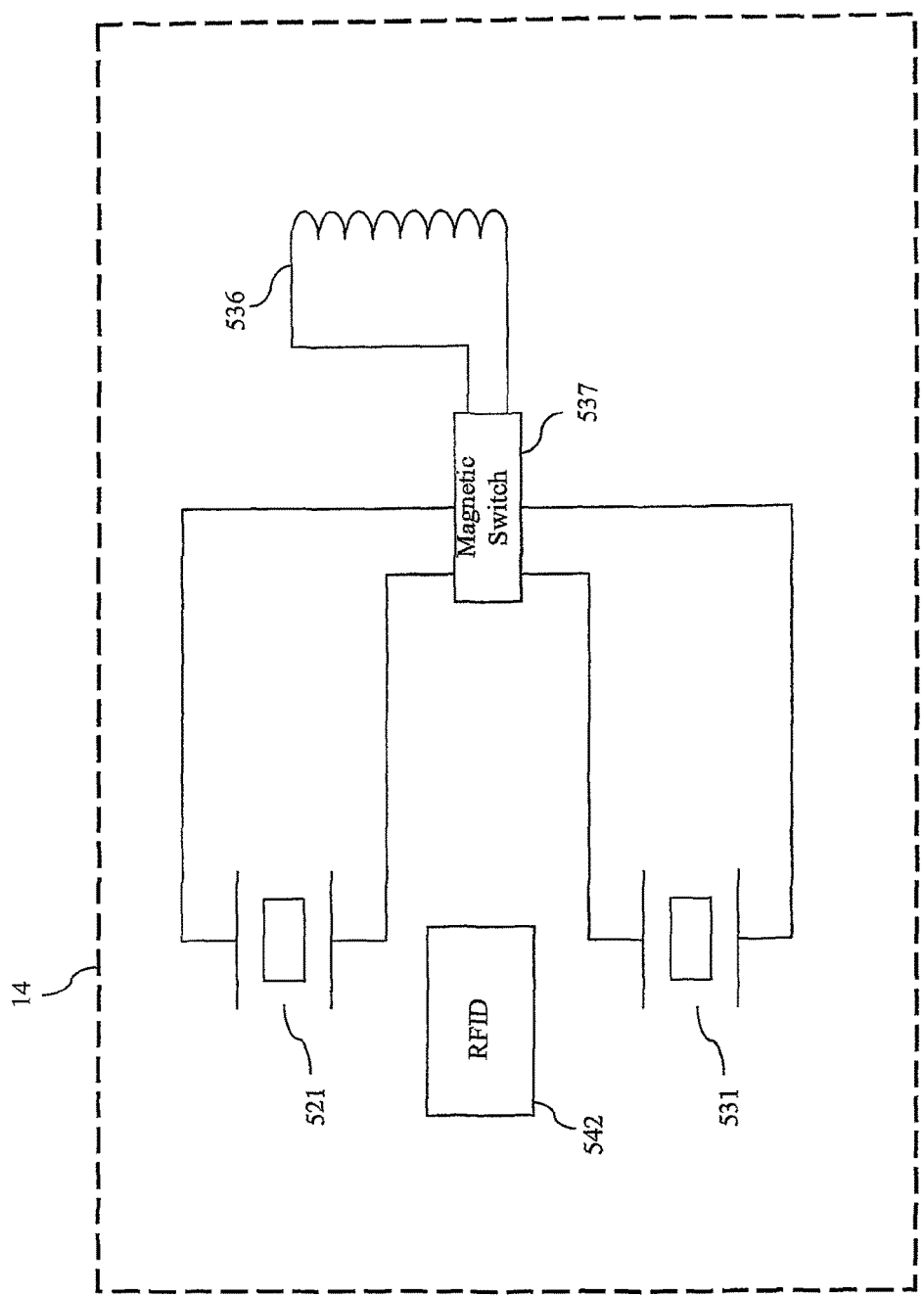
FIG. 18 is a circuit diagram of an alternate embodiment of the implant 14 where an inductive coil is shared between two crystal elements.

In an alternate embodiment of implant 14 shown in FIG. 18, a single inductive coil 536 is connected to magnetically controlled magnetic switch 537. Magnet switch 537 is connected to both sensor crystal 521 and reference crystal 531 so that when magnetic switch 537 is set, sensor crystal 521 is connected in series with inductive coil 536 and when magnetic switch 537 is reset, reference crystal 531 is connected in series with inductive coil 536.

The resonance frequencies $f_1$ of sensor circuit 520 and $f_0$ of reference circuit 530 are dependent upon the pressure experienced by sensor crystal 521 and reference crystal 531, respectively. The present invention functions to measure the resonant frequency difference, $f_0-f_1$, between the sensor circuit 520 and reference circuit 530 and through known relationships of resonance frequency difference and pressure change, calculate the absolute pressure within the given biological environment.

Sensor crystal 521 and reference crystal 531 consist of a synthetic piezoelectric crystal, such as lead-zirconate-titanate (PZT), shaped in a tubular configuration oriented along the crystalline x-axis. With appropriate electrical excitation, such a crystal will tend to oscillate in a "hoop" mode, wherein the radius of the tube expands and contracts over each cycle. The resonant oscillation frequency of the crystal is dependent upon the tube wall thickness and is highly stable as a function of time.

Piezoelectric crystals of this type have been successfully deployed in pressure measurement applications. The crystal's oscillation frequency decreases linearly due to loading when pressure is applied by a fluid to either the internal or external surface of the crystal. The crystal resonant oscillation frequency is a reproducible linear function of applied pressure. Fluidic coupling between suitably fabricated piezoelectric crystals and the brain parenchyma, or alternatively CSF, can allow accurate and reproducible transduction of intracranial pressure in a continuous or episodal way.

Incorporation of two tuned circuits into the implant 14 facilitates long-term measurement accuracy; in particular, resonantly tuned reference circuit 530 experiences the same long-term environmental changes as tuned sensor circuit 520. Tuned reference circuit 530 essentially compensates for resonant frequency changes associated with aging, temperature and stray capacitance.

In the preferred embodiment of the present invention, the sensor circuit and reference circuit are constructed with a cylindrical piezoelectric ceramic of about 20 mm total axial length, where 10 mm of length is used for the sensor section and the remaining 10 mm of length is used for reference section. The diameter of the cylinder is about 2 mm. The piezoelectric material is type P-6C and can be obtained from muRata Corporation of Nagaokakyo-shi, Kyoto, Japan. An alternate crystal supplier is Boston Piezo Optics, Inc. of Boston, Mass. The natural resonance of such a crystal is approximately 200 kHz. Sensor crystal 521 is put in series with inductor 525 of value 0.2 uH to create tuned resonant sensor circuit 520 with peak frequency of approximately 8

MHz and Q of about 2500. In another preferred embodiment, the crystal can have a diameter of about 6 mm with a wall thickness of 0.5 mm In the preferred embodiment, the operative parameters of inductive coils 525 and 535 are: implant coil diameter: 5 mm; implant coil width and thickness: 2 mm; implant coil turns: 10; implant coil inductance: 2e-7 Henries; and implant coil resistance: 0.004 ohm.

In the preferred embodiment, RF-ID tagging device 542 with non-volatile memory is incorporated into implant 14 to store calibration data as well as other relevant pre-stored data such as serial number, implant date and patient name. Microchip part number, MCRF452 is a suitable part for RF-ID tagging device 542, requiring connection to a single external inductive coil but no additional external capacitor. Said external inductive coil is also contained inside implant 14 but not shown in FIG. 14. Further useful details on deploying MCRF452 and similar RF-ID devices may be found in the Microchip MicroID® 13.57 MHz System Design Guide found at www.microchip.com.

Referring again to FIG. 14, the external coupling module 20 is comprised of "Dipper" circuit 430 connected to inductive coil 425 which operate together to sense the resonant frequencies of tuned sensor circuit 520 and tuned reference circuit 530, an analog to digital converter (ADC) 435 to measure dipper 430 output voltage, a voltage controlled oscillator (VCO) 460 in combination with a digital-to-analog converter (DAC) 455 to provide an excitation signal for "Dipper" circuit 430, a frequency counter 450 to measure the driving frequency from VCO 460, a receiver (RCVR) 445 for interrogating RF-ID devices, a microprocessor 440 for computation of pressure and for overall command and control of external coupling module 20, and a readout device 480 for displaying results.

The principle component of the external coupling module 20 is the "Dipper" circuit 430 which is known in the art as a "grid-dip" meter or "gate-dip" meter and well-known in the art of antenna and RF tuner calibration. "Dipper" circuit 430 functions to measure the RF energy absorption of a nearby tuned circuit. In the present invention, both the sensor circuit 520 and reference circuit 530 of implant 14 form the nearby tuned circuit. RF energy from "Dipper" circuit 430 is coupled to the tuned circuits of implant 14 via inductive coil 425.

Various schemes may be employed to scan the operating frequency of "Dipper" circuit 430. In the preferred embodiment of the present invention, microprocessor 440 digitally communicates a prescribed voltage to DAC 455 which generates output signal 458. VCO 460 accepts signal 458 and generates an oscillatory signal 465 at a known frequency ("Dipper" frequency) commensurate with signal 458 and outputs oscillatory signal 465 to drive "Dipper" circuit 430. A closed-loop frequency feedback is provided by frequency counter 450, so that microprocessor 440 reads the "Dipper" frequency from frequency counter 450 and adjusts DAC 455 to match the desired "Dipper" frequency. Microprocessor 440 may also log said frequency. The "Dipper" frequency is swept across the expected operating frequencies of the implant 14. Utilizing ADC 435, the analog "Dipper" amplitude 433 output of "Dipper" circuit 430 is converted to digital form 434. Microprocessor 440 accepts digital form 434 of "Dipper" amplitude 433 from ADC 435 and processes the data to effectively measure "Dipper" amplitude 433 as a function of "Dipper" frequency.

In an alternate embodiment, which operates open loop, DAC 455 is made to output a voltage ramp and microprocessor 440 in conjunction with frequency counter 450 logs the resulting "Dipper" frequency as a function of time. In a similar open-loop embodiment, DAC 455 is replaced by a suitable sawtooth voltage oscillator continuously operating at a frequency of about 10 Hz.

RCVR 445 reads pre-stored calibration data from RF-ID tagging device 542 and sends it to microprocessor 440 which uses said calibration data from the RF-ID tag along with the measured "Dipper" frequency and measured "Dipper" amplitude 433 to compute an ambient pressure sensed by implant 14 and exerted on sensor crystal 521. Microprocessor 440 formats the results appropriate for display and sends the data to readout device 480 via a flexible electrical cable 475. In one preferred embodiment, the readout device may be physically integrated with the external coupling module 20, as for example, a liquid crystal display (LCD) screen attached to it. In a second preferred embodiment, the readout device 480 is separated physically from external coupling module 20 and incorporated into a separate device (not shown) which also supplies power to external module 20 via flexible electrical cable 475, permanent data storage for permanently recording pressure as a function of time and an Ethernet network interface for continuous network monitoring of the patients intracranial pressure.

Figure 15A:
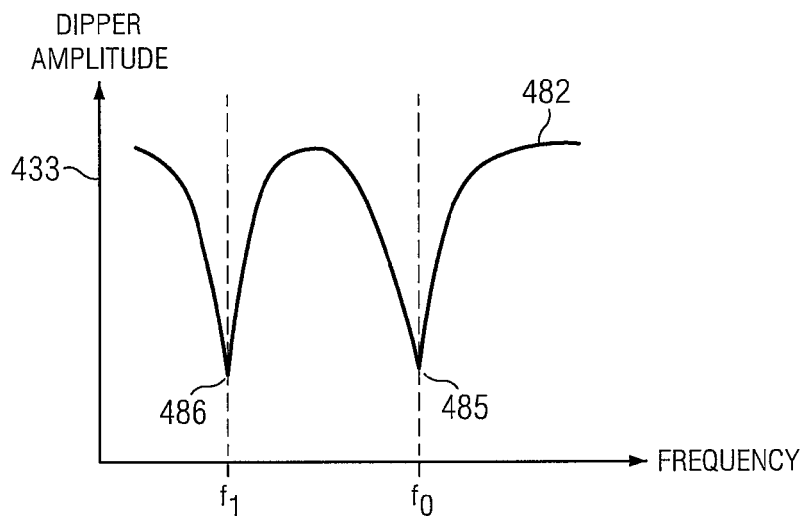
FIG. 15a is a graph of dipper amplitude versus frequency.
Figure 15B:
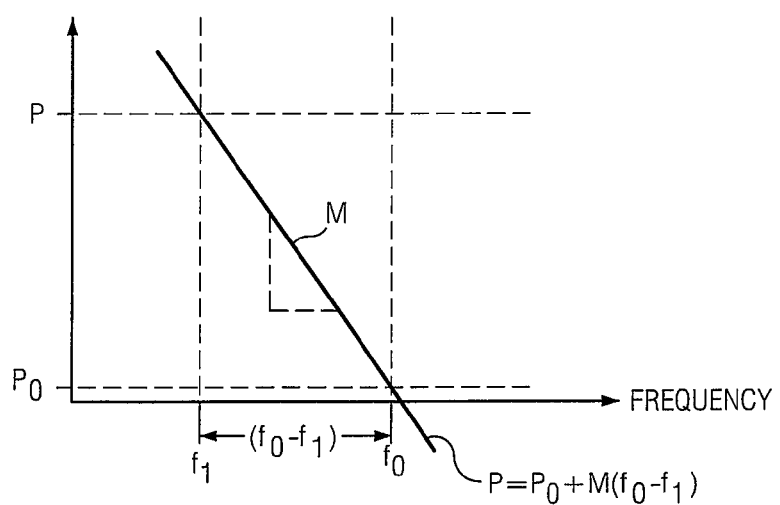
FIG. 15b is a graph of intracranial pressure versus frequency.

FIGS. 15a and 15b describe the method used by microprocessor 440 to compute intracranial pressure P. In FIG. 15a, measured "Dipper" amplitude 433 traces the absorption of RF energy by the tuned reference circuit 530 and the tuned sensor circuit 520. The dips in the frequency-amplitude function 482 correspond to the resonant frequencies of the implanted tuned circuits: the lower frequency dip 486 at frequency $f_1$ corresponds to the sensor circuit 520 at the intracranial pressure P, and the higher frequency dip 485 at frequency $f_0$ corresponds to reference circuit 530 at the reference pressure $P_0$. Microprocessor 440, under programmatic control, computes the frequency difference $(f_0-f_1)$ between the two minima of the frequency-amplitude function 482.

As shown in FIG. 15b, the intracranial pressure P applied to sensor crystal 521 is a decreasing linear function of the measured frequency difference $(f_0-f_1)$ and is calculated by microprocessor 440 according to the formula $P=P_0-m(f_0-f_1)$ where the slope m is determined by the specific geometry and physical characteristics of the sensor crystal 521 and $P_0$ is the pressured applied to the sealed reference crystal 531. The slope m is measured post-assembly and prior to subcutaneous insertion in a two-point calibration process. The slope m and fixed pressure $P_0$, resonant frequency $f_0$ and resonant frequency $f_1$ at ambient air pressure are calibration parameters recorded in the RF-ID tagging device 542.

In the alternate embodiment where magnetic switch 537 connects inductive coil 536 to either sensor crystal 521 or to reference crystal 531, magnetic switch 537 is first reset to connect only the reference crystal 531 to inductive coil 536. "Dipper" circuit 430 is scanned to read the resonant frequency $f_0$ and then magnetic switch 537 is set to connect sensor crystal 521 to inductive coil 536. "Dipper" circuit 430 is then scanned to read sensor frequency $f_1$. The difference $(f_0-f_1)$ is calculated and the pressure P computed from $P=P_0-m(f_0-f_1)$.

In the preferred embodiment of the present invention, a suitable choice for microprocessor 440 and ADC 435 is the Microchip part number PICHJ128GP306 which is a microcontroller that contains an onboard analog-to-digital converter (ADC), two on-board Universal Asynchronous transceivers (UARTs) for communications, an onboard pulse-width modulation (PWM) output for control, and several onboard timer counters. The onboard PWM of the PIC microcontroller may be used in conjunction with an external RC integrator to form digital-to-analog converter (DAC) 455. Frequency counter 450 may be realized by using one of the on-board timer counters of the PIC microcontroller with a suitable frequency divider. A suitable part for voltage-controlled oscillator (VCO) 460 is the 74HCT4046 phase locked loop (PLL) from Texas Instruments or a number of other semiconductor vendors. The output of the 74HCT4046 is typically buffered to achieve a 50 ohm drive capability. A suitable reference design for RCVR 445 can be found in the Microchip MicroID® 13.57 MHz System Design Guide located on the website www.microchip.com. Readout device 480 can be any number of LCD panels from a number of suppliers, an example being part number DMC20434N-EP made by Optrex Corporation.

Figure 14:
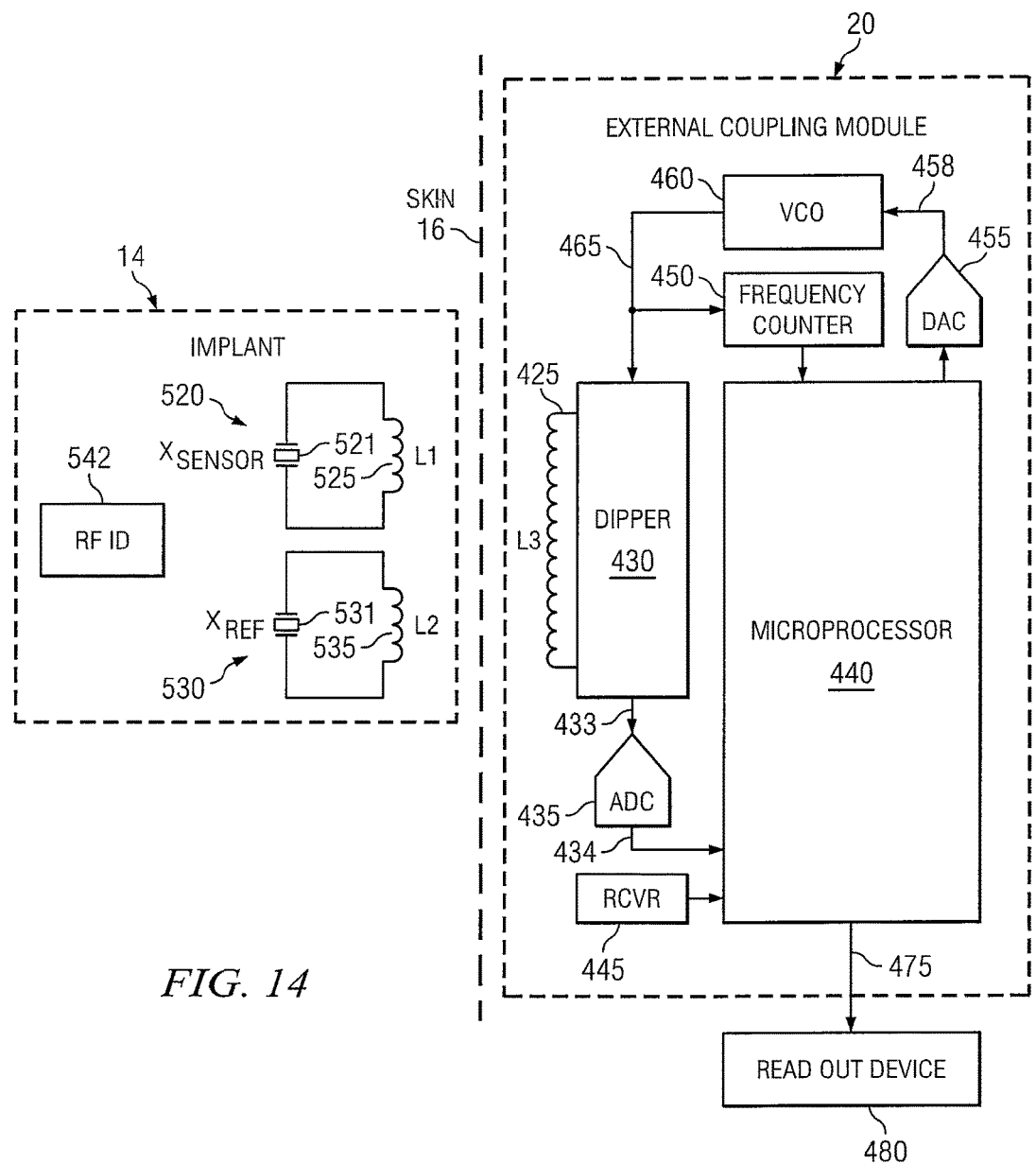
FIG. 14 is a schematic block diagram of a preferred embodiment of the invention.
Figure 16:
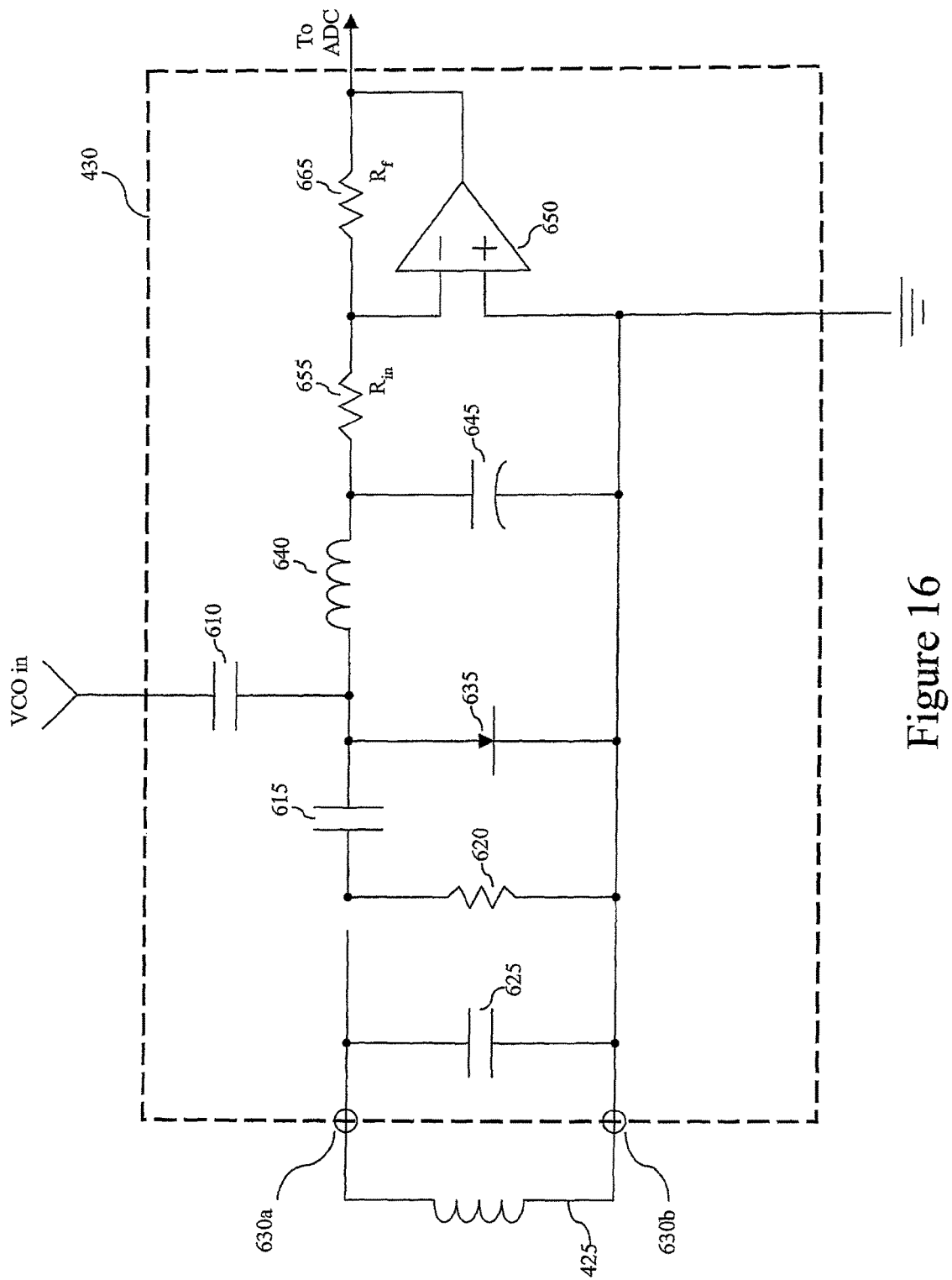
FIG. 16 is a schematic diagram of a dipper current of an embodiment of the present invention.

The preferred embodiment of "Dipper" circuit 430 is shown in the circuit diagram of FIG. 16. With reference then to FIGS. 14 and 16, VCO 460 RF output signal 465 is coupled into the circuit via coupling capacitor 610 and coupling capacitor 615. Resistor 620 acts to match the output impedance of VCO 460; both resistor 620 and VCO 460 output impedance act as a load to a resonant LC circuit comprised of capacitor 625 and inductor 425. Inductor 425 is a pluggable coil connected through electrical mount points 630*a* and 630*b* and positioned physically to maximize the electromagnetic field coupling to sensor circuit 520 and reference circuit 530. Inductor 425, capacitor 625 and resistor 620 are together tied to a common ground.

Diode 635 functions to produce a DC voltage in proportion to the RF signal current across inductor 425. Said DC voltage is transferred to the right half of "Dipper" circuit 430 through RF choke 640 which, in combination with bypass capacitor 645, effectively isolates high frequency RF signals from the DC amplifier part of the circuit near operational amplifier 650. Note that capacitor 615 functions to block DC voltage present at diode 635 from the resonant LC circuit and capacitor 610 functions to block said DC voltage from VCO 460. An inverting amplifier, comprised of input resistor 655 of resistance $R_i$, feedback resistor 665 of resistance $R_f$ and operational amplifier 650, amplifies the DC voltage generated by diode 635 to form the "Dipper" amplitude 433 which is a voltage sensed by ADC 435. The gain of said inverting amplifier is approximately the negative ratio of the feedback resistance 665 to the input resistance 655 and has a value $G = -R_f/R_i \sim 100$ to match the input dynamic range of ADC 435. Since the diode 635 DC voltage is nominally −40 mV, "Dipper" amplitude 433 is nominally 4 volts positive.

As the varying frequency of VCO 460 approaches one of the two resonances of sensor circuit 520 or reference circuit 530, the RF energy in the resonant LC circuit (of inductor 425 and capacitor 625) decreases and the DC voltage at diode 635 will drop correspondingly as will its amplified version "Dipper" amplitude 433.

In the preferred embodiment, inductor 425 and capacitor 635 are chosen to have values of 2 µH and 120 pF, typically. This provides for a reasonably broad resonance frequency response with a peak at 10 MHz and Q of 3 so that the resonance frequencies of the implanted devices may be readily scanned. Resistor 620 is nominally 50 ohm coinciding with the output impedance of VCO 460. Capacitor 615 is approximately 1000 pF and capacitor 610 is approximately 2000 pF. A 1N5711 Shottky barrier diode is a suitable choice for diode 635. RF choke 640 is nominally 2.2 mH and bypass electrolytic capacitor 645 is 0.1 µF. Resistor 655 is chosen to be 6.7 k-ohm while resistor 665 is 670 k-ohm for an inverting gain of 100. Operational amplifier 650 may be an inexpensive general purpose op-amp such as part number LM741CN from National Semiconductor.

In an alternate embodiment of the present invention the gain of the final DC amplifier section that produces "Dipper" amplitude 433 may be user programmable to easily accommodate varying coupling efficiencies between the implant 14 and the external module 20.

In the preferred embodiment, inductor 425 and capacitor 625 have typical values of approximately 2 uH and 250 pF. These selections provide for a reasonably broad resonance frequency response with a peak at 8 MHz and Q of 1.6 so that the resonance frequencies of the implanted sensor and reference circuits may be readily scanned.

Figure 17:
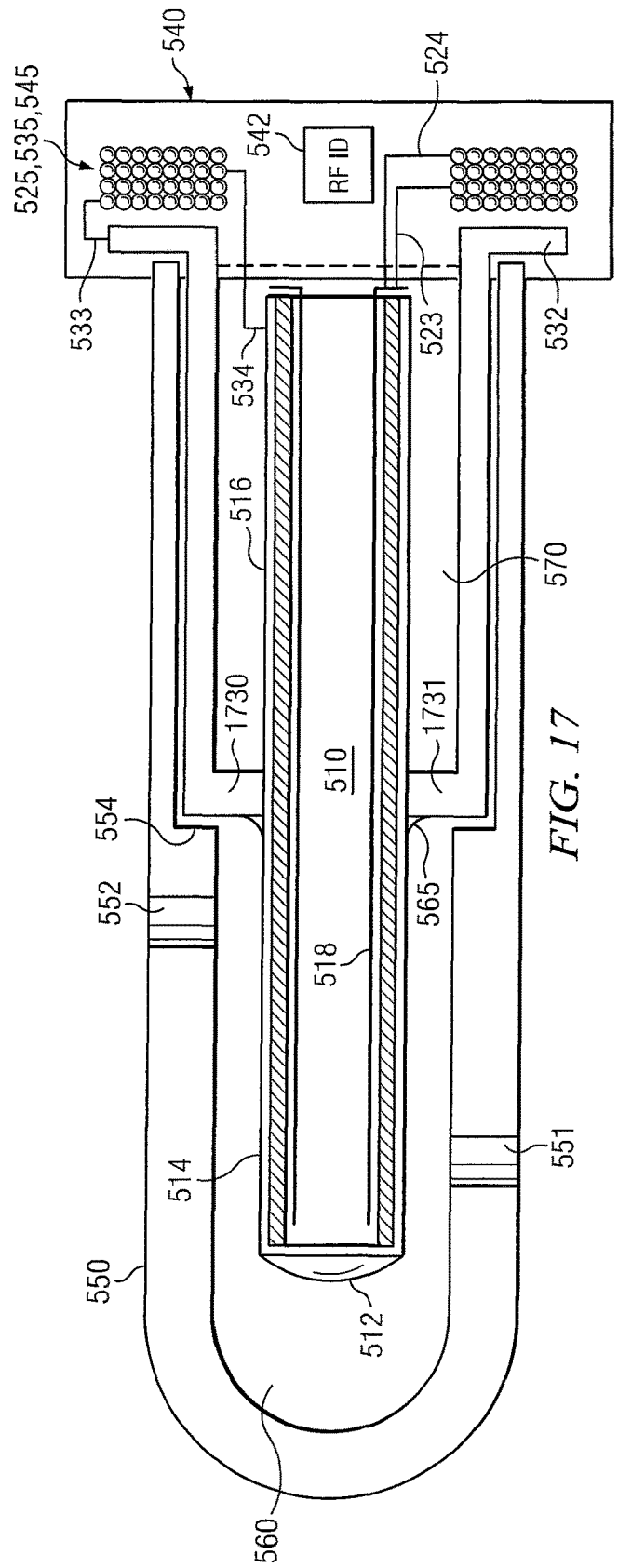
FIG. 17 is a cutaway view of the structure of a preferred embodiment of the invention.

Referring to FIG. 17, a preferred embodiment is shown. Epoxy endcap 540 comprises a housing for inductive coil 525 and inductive coil 535, and for interconnects 523, 524, 533 and 534 which function to interconnect the PZT substrate 510 electrically to said inductive coils. Epoxy endcap 540 also houses RF-ID tagging device 542 for identification purposes and a third inductive coil (not shown) which is connected to RF-ID device 542 for RF-ID powering and interrogation.

In the preferred embodiment, the epoxy endcap is a cylindrical container which can possess annular threads for use to secure the epoxy endcap in the skull.

External casing 550 and internal casing 1730 of implant 14 are constructed of a biocompatible metal such as titanium or alloy thereof or alternatively constructed of a biocompatible plastic. External casing 550 contains fluid ports 551 and 552 for allowing fluid to flow into and out of the ambient pressure cavity 560 so that said cavity is in pressure equilibrium with the intracranial fluid. Shoulder 554 is machined on the inside of external casing 550 about midway along its length. Internal casing 1730 is mounted inside external casing 550 against shoulder 554 and is held firmly in place by the epoxy endcap 540. Internal casing 1730 is gold sputtered which allows for the use of solder for electrical and mechanical attachment. PZT crystal substrate 510 is attached to internal casing 1730 by hermetically sealed fillet 565 and by solder. Alternatively, the internal casing 1730 may be composed of a biocompatible plastic which is hermetically sealed via hermetically sealed fillet 565. The metallization 514 may be extended as a small tab or short distance into reference cavity 570 to allow soldering of connector 533 directly to metallization 514. The external casing is cylindrical in form having a hemispherical dome opposite the epoxy endcap. The internal casing 1730 is generally cylindrical having a crystal support disc 1731 adjacent and supporting the center of the PZT crystal substrate 510. Internal casing 1730 also has a base support disc 532 which, when assembled, is secured within epoxy endcap 540. Hermetically sealed fillet 565 serves to rigidly connect crystal support disc 1731 and PZT crystal substrate 510.

The tubular shaped PZT crystal 510 is metalized to form two functionally independent resonating devices, namely the reference crystal 531 and the sensor crystal 521. The sensor crystal 521 is formed in contact with ambient pressure cavity 560 while the reference crystal 531 is formed in contact with reference cavity 570. The interior surface of PZT crystal 510 is metalized along its entire length with a common metallization layer 518. Wire leads are soldered directly to common metallization layer 518 and are connected to inductive coil 525 and inductive coil 535 via interconnects 523 and 524, respectively. Endcap 540 may be hermetically sealed to the PZT crystal substrate 510 so that the ambient pressure applies only to the external surface of the PZT crystal. The interior of the PZT crystal is at the same pressure as the reference pressure cavity 570 in the preferred embodiment of the present invention.

The exterior surface of PZT crystal 510 is metalized in two segments: a first segment, transducer metallization layer 514, which extends from endcap 512 to the vicinity of shoulder 554 and a second segment reference metallization layer 516, which extends from the rightmost end (as shown in FIG. 17) of PZT crystal 510 near epoxy endcap 540 to the vicinity of internal casing 1730, reference metallization layer 516 being etched so that it does not come into electrical contact with internal casing 1730 or transducer metallization layer 514.

Transducer metallization layer 514 is in contact with internal casing 1730 so that an electrically conductive path exists from transducer metallization layer 514 along the internal casing 1730 into the vicinity of the epoxy endcap 540. Interconnect 533 connects transducer inductive coil 525 to internal casing 1730 and thus to the transducer metallization layer 514. Interconnect 534 is soldered to reference metallization 516 and connected to inductive coil 535. In an alternate embodiment where the internal casing 1730 and external casing 550 are both made of biocompatible plastic material and hermetically sealed via hermetically sealed fillet 565, the metallization 514 may be extended as a small tab a short distance into reference cavity 570 to allow soldering of interconnect 533 directly to metallization 514.

Gold is utilized for metallization to provide biocompatibility and minimize deposition of bioproteins on the sensor. Wire leads may be soldered directly to the metalized layer. Hermetic seals may be composed of medical grade epoxy, silicone or other suitable material.

In the preferred embodiment of the present invention, external coupling module 20 is located on a printed circuit board (PCB) in a molded plastic housing which also houses inductive coil 425 and readout device 480, an LCD panel attached to the given PCB circuit board. A holder for batteries and power-on button are included with said molded plastic housing. When powered, microprocessor 440 boots up and then automatically operates to scan the "Dipper" amplitude 433 and locate nearby resonant circuits. Molded plastic housing has tabs for placing the unit onto the patient's head and securing with straps or with tape.

In practice, microprocessor 440 scans the dipper frequencies by first sending the appropriate signals to excite the transducer section and reference section via inductive coil 425. The frequency absorption of the transducer section and the reference section of the PZT crystal substrate are then measured and compared to determine a frequency difference. The frequency difference is relayed to the microprocessor which then relates the difference in frequency to the reference pressure to determine the intracranial fluid pressure according to the equation $P=P0-m(f_0-f_1)$ as previously described.

Additionally, the microprocessor is programmed to store a set of calibrated data in the memory of the RF-ID tagging device 542 including the initial reference pressure, the initial intracranial pressure and the initial calibration slope. The microprocessor is also programmed to store a set of patient data in the memory of the RF-ID tag and device such as name, social security number, relevant medical conditions and other relevant patient data. Empirical equations or tables relating protein deposits to crystal resonant frequency may also be stored in the RF-ID tag.

Figure 19:
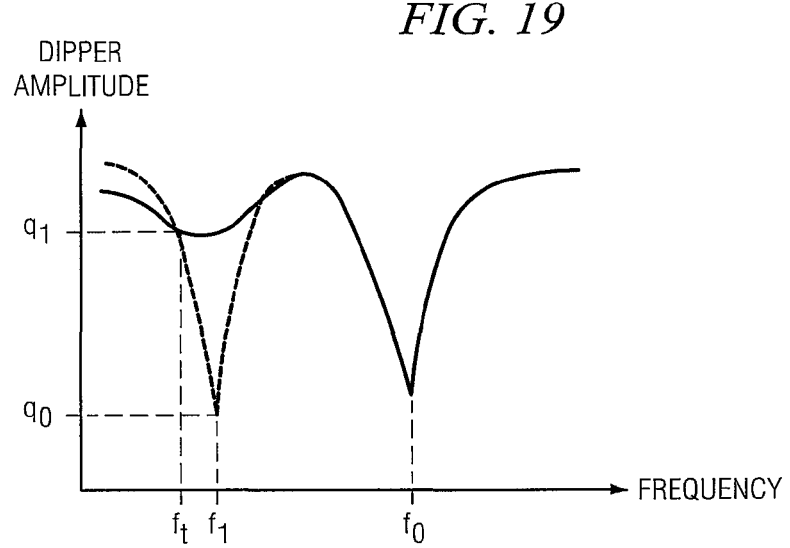
FIG. 19 is a graph of dipper amplitude versus frequency accounting for protein deposits.

In an alternate embodiment, the microprocessor can be configured to compensate for protein deposits as follows. In practice, the ICP sensor can be implanted in a patient for many years. Since the transducer crystal is physically exposed to intracranial fluid during this entire period of time, a protein buildup is expected on its surface. The protein buildup serves to slow the vibration of the transducer crystal and increase the power required to accomplish oscillation. Referring to FIG. 19, the local minimum of the sensor $q_0$ can be seen to increase from $q_0$ to $q_1$ after an elapsed period of time, $t_{elapsed}$ due to protein deposits. Further, FIG. 19 shows that the frequency of the sensor drifts from $f_1$ to $f_t$ due to the same phenomenon.

Figure 20:
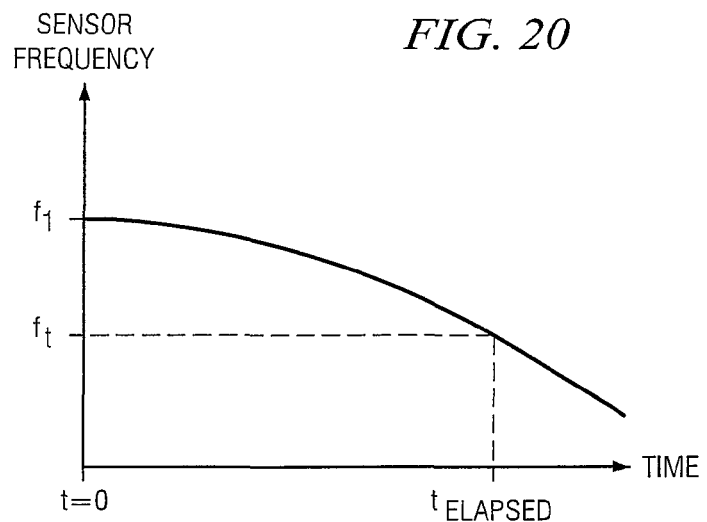
FIG. 20 is a graph of sensor frequency versus elapsed time accounting for protein deposits.

Referring to FIG. 20, a graph showing sensor frequency versus time according to protein deposits is shown. At initial time $t_0$, a local minimum sensor frequency $f_1$ is shown. After an elapsed time is equal to $t_{elapsed}$ a frequency shift to $f_t$ is shown. An empirical equation can be derived for any time t to report a frequency shift $f_t f_t$. The microprocessor is programmed to report a frequency $f_r$ according to the equation $f_{reported} = f_{measured} + (f_1 - f_t)$; where $f_{measured}$ is the frequency minimum reported by the dipper circuit, $f_1$ is the initial local minimum of the sensor and $f_t$ is the frequency derived from the elapsed time sensor frequency curve stored in the microprocessor. A lookup table for an empirical equation can be employed by the microprocessor to arrive at $f_t$ given $t_{elapsed}$.

In order to derive to $t_{elapsed}$, the microprocessor stores the initial date and time of the implant of the ICP sensor in the patient in RF-ID tagging device 542 as initial time $t_0$. When the system is initiated and readings are taken after implant, the microprocessor subtracts $t_0$ from the current date and time to arrive at $t_{elapsed}$.

In a second embodiment of the housing for the present invention, the display device and power supply is contained in a separate instrument housing connected to external coupling module 20, itself housed on a PCB circuit board in a molded plastic housing along with inductive coil 425 and readout device 480. Said instrument housing is connected via a cable with wires sufficient for power and for a serial interface, the latter being connected to an onboard UART built into microprocessor 440 for serial communications. A permanent storage device, such as hard drive, CD R/W or DVD R/W is included in the instrument housing which also has an Ethernet network interface for network-based monitoring of intracranial pressure.

While the present invention has been described in terms of specific embodiments thereof, it will be understood in view of the present disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

The invention claimed is:

1. A method of collecting data from a device implanted in an organism, the method executed by an electronic circuit of the implanted device, the method comprising the steps of:
   activating, with an inductively coupled power source, the implanted device;
   generating, with an electrically activated variable oscillator, a data signal in response to a physical parameter of the organism;
   comparing, with a transistor, the data signal to a reference signal to produce an intermediate signal;
   encoding, with a diode, the intermediate signal into a first near infrared signal that is transmitted from the implanted device; and, transmitting, with the diode, the first near infrared signal through a transducer crystal connected to the electrically activated variable oscillator.

2. The method of claim 1 wherein the step of activating comprises the further steps of;
generating an electromagnetic power signal by an extracorporeal device; and,
receiving the electromagnetic power signal by the implanted device.

3. The method of claim 1 wherein the step of generating comprises the further steps of:
altering a parameter of an electrical semiconductor device; and,
deriving the data signal from the altered parameter.

4. The method of claim 1 wherein the step of encoding comprises the further step of creating a pulse width modulated signal.

5. The method of claim 1 wherein the step of encoding comprises the further step of creating a frequency modulated signal.

6. The method of claim 1 further comprising:
generating, with an electrically activated reference oscillator, the reference signal.

7. The method of claim 6 further comprising:
generating, with a heterodyne amplifier, the intermediate signal.

8. The method of claim 7 further comprising:
generating, with a low pass filter and level detector, a digital signal from the intermediate signal that is based on a beat frequency between the data signal and the reference signal.

9. The method of claim 8 further comprising:
generating, with a monostable multivibrator, a pulse that is based on the digital signal.

10. The method of claim 9 further comprising:
modulating, with a driver, a near infrared (NIR) emitter diode based on the pulse to generate the near infrared signal.

11. The method of claim 1, further comprising:
transmitting the first near infrared signal through the transducer crystal and a silastic dome.

12. The method of claim 11, further comprising:
providing the silastic dome on a first side of the transducer crystal.

13. A method of collecting data from a device implanted in an organism, the method executed by an electronic circuit of the implanted device, the method comprising the steps of:
activating, with an inductively coupled power source, the implanted device;
generating with an electrically activated variable oscillator, a data signal in response to a physical parameter of the organism;
comparing, with a transistor, the data signal to a reference signal to produce an intermediate signal;
encoding, with a diode, the intermediate signal into a first near infrared signal that is transmitted from the implanted device;
transmitting, with the diode, the first near infrared signal through a transducer crystal connected to the electrically activated variable oscillator;
transmitting the first near infrared signal through the transducer crystal and a silastic dome;
providing the silastic dome on a first surface of the transducer crystal;
providing an integrated monolithic circuit, which includes the diode, on a second surface of the transducer crystal;
wherein the first surface is opposite from the second surface;
providing the integrated monolithic circuit between the transducer crystal and a reference crystal connected to an electrically activated reference oscillator; and,
providing the transducer crystal between the silastic dome and the integrated monolithic circuit.

\* \* \* \* \*